US007682318B2

(12) United States Patent  
Alden et al.

(10) Patent No.: US 7,682,318 B2
(45) Date of Patent: *Mar. 23, 2010

(54) BLOOD SAMPLING APPARATUS AND METHOD

(75) Inventors: Don Alden, Sunnyvale, CA (US); Dominique M. Freeman, La Honda, CA (US); Paul Lum, Los Altos, CA (US); Vladimir Drbal, Belmont, CA (US); Catherine K. Templin, Portola Valley, CA (US); Dirk Boecker, Palo Alto, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 1125 days.

This patent is subject to a terminal disclaimer.

(21) Appl. No.: 10/363,508

(22) PCT Filed: Jun. 12, 2002

(86) PCT No.: PCT/US02/19054

§ 371 (c)(1),
(2), (4) Date: Sep. 3, 2003

(87) PCT Pub. No.: WO02/100252

PCT Pub. Date: Dec. 19, 2002

(65) Prior Publication Data

US 2005/0101979 A1    May 12, 2005

(51) Int. Cl.
    *A61B 5/00*    (2006.01)
(52) U.S. Cl. ..................... 600/583; 606/181
(58) Field of Classification Search ........... 600/578, 600/582, 583, 584; 606/181–184; 604/115
    See application file for complete search history.

(56) References Cited

U.S. PATENT DOCUMENTS

| 2,714,890 A | 8/1955 | Vang .................... 128/305 |
| 2,801,633 A | 8/1957 | Mauze et al. |
| 3,086,288 A | 4/1963 | Balamuth et al. ........... 30/272 |
| 3,208,452 A | 9/1965 | Stern ..................... 128/315 |
| 3,358,689 A | 12/1967 | Higgins .................. 128/329 |
| 3,494,358 A | 2/1970 | Grossenbacher ........... 128/218 |

(Continued)

FOREIGN PATENT DOCUMENTS

DE    4420232    12/1995

(Continued)

OTHER PUBLICATIONS

International Search Report (PCT/ISA/220) for PCT/US02/19058.

(Continued)

*Primary Examiner*—Michael J Milano
*Assistant Examiner*—Victor X Nguyen
(74) *Attorney, Agent, or Firm*—Paul Davis; Goodwin Procter LLP

(57) ABSTRACT

Blood samples can be collected without substantial contamination from ambient air, such that the blood sample may be analyzed accurately for gaseous components such as oxygen and carbon dioxide. An embodiment of the device has integrated actuation, lancing, and sample acquisition components, which in some embodiments are miniaturized and/or disposable.

16 Claims, 4 Drawing Sheets

U.S. PATENT DOCUMENTS

| | | | |
|---|---|---|---|
| 3,626,929 A | 12/1971 | Sanz | 128/2 R |
| 3,673,475 A | 6/1972 | Britton, Jr. | 318/122 |
| 3,742,954 A | 7/1973 | Strickland | 128/302 |
| 3,832,776 A | 9/1974 | Sawyer | 30/272 |
| 3,953,172 A | 4/1976 | Shapiro | 23/230 |
| 4,077,406 A | 3/1978 | Sandhage et al. | 128/217 |
| 4,154,228 A | 5/1979 | Feldstein et al. | 128/329 |
| 4,203,446 A | 5/1980 | Höfert et al. | 128/329 |
| 4,223,674 A | 9/1980 | Fluent et al. | 128/217 |
| 4,224,125 A | 9/1980 | Nakamura | 204/195 B |
| 4,230,118 A | 10/1980 | Holman et al. | 128/314 |
| 4,338,174 A | 7/1982 | Tamura | 204/195 |
| 4,340,669 A | 7/1982 | Bauer | 435/14 |
| 4,353,984 A | 10/1982 | Yamada | 435/14 |
| 4,356,826 A | 11/1982 | Kubota | 128/630 |
| 4,360,016 A | 11/1982 | Sarrine | 128/763 |
| 4,391,905 A | 7/1983 | Bauer | 435/14 |
| 4,391,906 A | 7/1983 | Bauer | 435/14 |
| 4,414,975 A | 11/1983 | Ryder | 128/314 |
| 4,420,564 A | 12/1983 | Tsuji | 435/288 |
| 4,426,451 A | 1/1984 | Columbus | 436/518 |
| 4,426,884 A | 1/1984 | Polchaninoff | 73/172 |
| 4,449,529 A | 5/1984 | Burns et al. | 128/314 |
| 4,462,405 A | 7/1984 | Ehrlich | 128/329 |
| 4,469,110 A | 9/1984 | Slama | 128/770 |
| 4,517,978 A | 5/1985 | Levin | 128/314 |
| 4,518,384 A | 5/1985 | Tarello et al. | 604/61 |
| 4,535,773 A | 8/1985 | Yoon | 604/51 |
| 4,539,988 A | 9/1985 | Shirley | 128/314 |
| 4,545,382 A | 10/1985 | Higgins | 128/635 |
| 4,553,541 A | 11/1985 | Burns et al. | 128/314 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,590,411 A | 5/1986 | Kelly | 318/687 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A | 12/1986 | Garcia et al. | 128/770 |
| 4,637,393 A | 1/1987 | Ray | 128/305 |
| 4,637,403 A | 1/1987 | Garcia et al. | 128/770 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,653,513 A * | 3/1987 | Dombrowski | 600/578 |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,750,489 A | 6/1988 | Berkman et al. | 128/314 |
| 4,758,323 A | 7/1988 | Davis | 204/403 |
| 4,787,398 A | 11/1988 | Garcia et al. | 128/770 |
| 4,794,926 A | 1/1989 | Munsch et al. | 128/314 |
| 4,814,142 A | 3/1989 | Gleisner | 422/56 |
| 4,814,661 A | 3/1989 | Ratzlaff | 310/328 |
| 4,820,010 A | 4/1989 | Sciefres | 385/43 |
| 4,820,399 A | 4/1989 | Senda | 204/403 |
| 4,823,806 A | 4/1989 | Bajada | 128/744 |
| 4,824,639 A | 4/1989 | Hildenbrand | 422/56 |
| RE32,922 E | 5/1989 | Levin et al. | 128/314 |
| 4,827,763 A | 5/1989 | Bourland | 73/172 |
| 4,830,959 A | 5/1989 | McNeill | 435/53 |
| 4,836,904 A | 6/1989 | Armstron | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,895,156 A | 1/1990 | Schulze | 128/634 |
| 4,897,173 A | 1/1990 | Nankai | 204/403 |
| 4,900,424 A | 2/1990 | Birth et al. | 204/409 |
| 4,911,794 A | 3/1990 | Parce | 204/1 T |
| 4,920,977 A | 5/1990 | Haynes | 128/770 |
| 4,924,879 A | 5/1990 | O'Brien | 128/770 |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | 606/181 |
| 4,990,154 A | 2/1991 | Brown | 606/182 |
| 4,995,402 A | 2/1991 | Smith et al. | 128/771 |
| 4,999,582 A | 3/1991 | Parks | 324/438 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| 5,029,583 A | 7/1991 | Meserol et al. | 128/633 |
| 5,035,704 A | 7/1991 | Lambert et al. | 606/182 |
| 5,047,044 A | 9/1991 | Smith et al. | 606/182 |
| 5,054,499 A | 10/1991 | Swierczek | 128/770 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,097,810 A | 3/1992 | Fishman et al. | 128/743 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | De Castro | 422/56 |
| 5,108,564 A | 4/1992 | Szuminsky | 204/153.12 |
| 5,108,889 A | 4/1992 | Smith et al. | |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | De Castro | 210/767 |
| 5,141,868 A | 8/1992 | Shanks | 435/288 |
| 5,145,565 A | 9/1992 | Kater et al. | 204/153.1 |
| 5,152,775 A | 10/1992 | Ruppert | 606/182 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown | D24/146 |
| 5,178,142 A | 1/1993 | Harjunmaa | 128/633 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,188,118 A | 2/1993 | Terwilliger | 128/753 |
| 5,189,751 A | 3/1993 | Giuliani et al. | 15/22.1 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |

| Patent No. | Kind | Date | Inventor | Class |
|---|---|---|---|---|
| 5,205,920 | A | 4/1993 | Oyama | 204/403 |
| 5,212,879 | A | 5/1993 | Biro | 29/437 |
| 5,216,597 | A | 6/1993 | Beckers | 364/413.02 |
| 5,217,480 | A | 6/1993 | Haber | 606/182 |
| 5,222,504 | A | 6/1993 | Solomon | 128/744 |
| 5,228,972 | A | 7/1993 | Osaka | 204/415 |
| 5,229,282 | A | 7/1993 | Yoshioka | 435/177 |
| 5,230,866 | A | 7/1993 | Shartle | 422/103 |
| 5,231,993 | A | 8/1993 | Haber et al. | 128/770 |
| 5,250,066 | A | 10/1993 | Lambert | 606/181 |
| 5,251,126 | A | 10/1993 | Kahn | 364/413.11 |
| 5,253,656 | A | 10/1993 | Rincoe | 128/782 |
| 5,256,998 | A | 10/1993 | Becker | 335/229 |
| 5,264,103 | A | 11/1993 | Yoshioka | 204/403 |
| 5,264,105 | A | 11/1993 | Gregg | 204/403 |
| 5,264,106 | A | 11/1993 | McAleer | 204/403 |
| 5,266,179 | A | 11/1993 | Nankai | 204/401 |
| D342,673 | S | 12/1993 | Kataoka | D24/147 |
| 5,272,087 | A | 12/1993 | El Murr | 435/291 |
| 5,277,181 | A | 1/1994 | Mendelson | 128/633 |
| 5,279,294 | A | 1/1994 | Anderson et al. | 128/633 |
| 5,282,822 | A | 2/1994 | Macors | 606/182 |
| 5,286,362 | A | 2/1994 | Hoenes | 204/403 |
| 5,286,364 | A | 2/1994 | Yacynych | 204/418 |
| 5,288,636 | A | 2/1994 | Pollmann | 435/288 |
| 5,304,192 | A | 4/1994 | Crouse | 606/181 |
| 5,304,193 | A | 4/1994 | Zhadanov | 606/182 |
| 5,312,590 | A | 5/1994 | Gunasingham | 422/56 |
| 5,314,441 | A | 5/1994 | Cusack | 606/182 |
| 5,314,442 | A | 5/1994 | Morita | 606/182 |
| 5,316,012 | A | 5/1994 | Siegal | 128/744 |
| 5,318,583 | A | 6/1994 | Rabenau et al. | 606/182 |
| 5,320,607 | A | 6/1994 | Ishibashi | 604/115 |
| 5,320,808 | A | 6/1994 | Holen et al. | 422/64 |
| 5,324,302 | A | 6/1994 | Crouse | 606/181 |
| 5,324,303 | A | 6/1994 | Strong | 606/181 |
| 5,332,479 | A | 7/1994 | Uenoyama | 204/153.12 |
| 5,350,392 | A | 9/1994 | Purcell | 606/182 |
| 5,352,351 | A | 10/1994 | White | 204/406 |
| 5,354,287 | A | 10/1994 | Wacks | 604/232 |
| 5,354,447 | A | 10/1994 | Uenoyama | 204/403 |
| 5,356,420 | A | 10/1994 | Czernecki | 606/182 |
| 5,360,410 | A | 11/1994 | Wacks | 604/232 |
| 5,366,469 | A | 11/1994 | Steg | 606/182 |
| 5,366,470 | A | 11/1994 | Ramel | 606/183 |
| 5,366,609 | A | 11/1994 | White | 204/403 |
| 5,368,047 | A | 11/1994 | Suzuki et al. | 128/765 |
| 5,371,687 | A | 12/1994 | Holmes | 364/514 |
| 5,375,397 | A | 12/1994 | Ferrand | 54/66 |
| 5,378,628 | A | 1/1995 | Graetzel | 435/288 |
| 5,382,346 | A | 1/1995 | Uenoyama | 204/403 |
| 5,383,885 | A | 1/1995 | Bland | 606/182 |
| 5,389,534 | A | 2/1995 | Gentezkow | 435/180 |
| 5,393,903 | A | 2/1995 | Graetzel | 556/137 |
| 5,395,387 | A | 3/1995 | Burns | 606/181 |
| 5,397,334 | A | 3/1995 | Schenk | 606/182 |
| 5,401,376 | A | 3/1995 | Foos | 204/415 |
| 5,402,798 | A | 4/1995 | Swierczek | 128/633 |
| 5,405,511 | A | 4/1995 | White | 204/153.1 |
| 5,407,545 | A | 4/1995 | Hirose | 204/153.12 |
| 5,407,554 | A | 4/1995 | Saurer | 204/403 |
| 5,407,818 | A | 4/1995 | Gentezkow | 435/180 |
| 5,409,583 | A | 4/1995 | Yoshioka | 204/153.12 |
| 5,409,664 | A | 4/1995 | Allen | |
| 5,410,059 | A | 4/1995 | Fraser | 546/10 |
| 5,415,169 | A | 5/1995 | Siczek et al. | 128/653.1 |
| 5,423,847 | A | 6/1995 | Strong et al. | 606/182 |
| 5,436,161 | A | 7/1995 | Bergstrom | 435/291 |
| 5,437,999 | A | 8/1995 | Diebold | 435/288 |
| 5,438,271 | A | 8/1995 | White | 324/444 |
| 5,443,701 | A | 8/1995 | Willner | 204/153 |
| 5,445,920 | A | 8/1995 | Saito | 430/311 |
| D362,719 | S | 9/1995 | Kaplan | D24/147 |
| 5,454,828 | A | 10/1995 | Schraga | 606/181 |
| 5,456,875 | A | 10/1995 | Lambert | 264/328.1 |
| 5,464,418 | A | 11/1995 | Schraga | 606/182 |
| 5,471,102 | A | 11/1995 | Becker | 310/50 |
| 5,472,427 | A | 12/1995 | Rammler | 604/164 |
| 5,474,084 | A | 12/1995 | Cunniff | 128/744 |
| 5,476,474 | A | 12/1995 | Davis | 606/182 |
| 5,480,387 | A | 1/1996 | Gabriel | 604/134 |
| 5,487,748 | A | 1/1996 | Marshall | 606/182 |
| 5,496,453 | A | 3/1996 | Uenoyama | 205/777.5 |
| 5,498,542 | A | 3/1996 | Corey | 435/283.1 |
| 5,507,288 | A | 4/1996 | Bocker | 128/633 |
| 5,508,171 | A | 4/1996 | Walling | 205/777.5 |
| 5,509,410 | A | 4/1996 | Hill | 128/637 |
| 5,510,266 | A | 4/1996 | Bonner et al. | 436/43 |
| 5,512,159 | A | 4/1996 | Yoshioka | 204/403 |
| 5,514,152 | A | 5/1996 | Smith | 606/182 |
| 5,518,006 | A | 5/1996 | Mawhirt | 128/770 |
| 5,524,636 | A | 6/1996 | Sarvazyan | 128/774 |
| 5,525,511 | A | 6/1996 | D'Costa | 435/287.9 |
| 5,527,333 | A | 6/1996 | Nikkels | 606/182 |
| 5,527,334 | A | 6/1996 | Kanner | 606/182 |
| 5,529,074 | A | 6/1996 | Greenfield | 128/744 |
| 5,540,709 | A | 7/1996 | Ramel | 606/183 |
| 5,543,326 | A | 8/1996 | Heller et al. | 435/287.9 |
| 5,545,174 | A | 8/1996 | Schenk | 606/182 |
| 5,547,702 | A | 8/1996 | Gleisner | 427/2.13 |
| 5,554,166 | A | 9/1996 | Lange | 606/182 |
| 5,558,834 | A | 9/1996 | Chu | 422/55 |
| 5,569,286 | A | 10/1996 | Peckham | 606/181 |
| 5,569,287 | A | 10/1996 | Tezuka | 606/182 |
| 5,571,132 | A | 11/1996 | Mawhirt | 606/182 |
| 5,575,403 | A | 11/1996 | Charlton et al. | 221/31 |
| 5,575,895 | A | 11/1996 | Ikeda | 204/403 |
| 5,582,697 | A | 12/1996 | Ikeda | 204/403 |
| 5,584,846 | A | 12/1996 | Mawhirt | 606/181 |
| 5,593,852 | A | 1/1997 | Heller | 435/14 |
| 5,599,501 | A | * | 2/1997 | Carey et al. | 422/64 |
| 5,609,749 | A | 3/1997 | Yamauchi | 205/777.5 |
| 5,613,978 | A | 3/1997 | Harding | 606/181 |
| 5,620,579 | A | 4/1997 | Genshaw | 204/402 |
| 5,624,537 | A | 4/1997 | Turner | 204/403 |
| D379,516 | S | 5/1997 | Rutter | D24/146 |
| 5,628,764 | A | 5/1997 | Schraga | 606/182 |
| 5,628,765 | A | 5/1997 | Morita | 606/182 |
| 5,628,890 | A | 5/1997 | Carter | 204/403 |
| 5,630,986 | A | 5/1997 | Charlton et al. | 422/64 |
| 5,632,410 | A | 5/1997 | Moulton et al. | 221/79 |
| 5,640,954 | A | 6/1997 | Pfeiffer | 128/635 |
| 5,643,306 | A | 7/1997 | Schraga | 606/182 |
| 5,645,555 | A | 7/1997 | Davis | 606/182 |
| 5,650,062 | A | 7/1997 | Ikeda | 205/778 |
| 5,653,863 | A | 8/1997 | Genshaw | 205/777.5 |
| 5,657,760 | A | 8/1997 | Ying et al. | 128/660.03 |
| 5,658,444 | A | 8/1997 | Black | 204/415 |
| 5,662,127 | A | 9/1997 | De Vaughn | 128/765 |
| 5,662,672 | A | 9/1997 | Pambianchi | 606/181 |
| 5,676,143 | A | 10/1997 | Simonsen | 128/633 |
| 5,680,858 | A | 10/1997 | Hansen | 128/635 |
| 5,680,872 | A | 10/1997 | Sesekura | 128/760 |
| 5,682,884 | A | 11/1997 | Hill | 128/637 |
| 5,683,562 | A | 11/1997 | Schaffar | 204/403 |
| 5,695,947 | A | 12/1997 | Guo | 435/11 |
| 5,700,695 | A | 12/1997 | Yassinzadeh et al. | 436/180 |
| 5,705,045 | A | 1/1998 | Park | 204/403 |
| 5,708,247 | A | 1/1998 | McAleer | 204/403 |
| 5,709,668 | A | 1/1998 | Wacks | 604/232 |
| 5,709,699 | A | 1/1998 | Warner | 606/181 |
| 5,710,011 | A | 1/1998 | Forrow | 435/25 |
| 5,714,390 | A | 2/1998 | Hallowitz et al. | 436/526 |
| 5,720,862 | A | 2/1998 | Hamamoto | 204/403 |
| 5,720,924 | A | 2/1998 | Eikmeier et al. | 422/102 |
| D392,391 | S | 3/1998 | Douglas | D24/225 |

| | | | |
|---|---|---|---|
| 5,723,284 A | 3/1998 | Ye .................................. 435/4 |
| 5,727,548 A | 3/1998 | Hill ............................ 128/637 |
| 5,730,753 A | 3/1998 | Morita ........................ 606/181 |
| 5,733,300 A | 3/1998 | Pambianchi ................. 606/181 |
| D393,716 S | 4/1998 | Brenneman ................. D24/147 |
| D393,717 S | 4/1998 | Brenneman ................. D24/147 |
| 5,738,244 A | 4/1998 | Charlton et al. ............... 221/26 |
| 5,741,228 A | 4/1998 | Lambrecht .................. 604/93 |
| 5,741,634 A | 4/1998 | Nozoe ........................... 435/4 |
| RE35,803 E | 5/1998 | Lange .......................... 606/182 |
| 5,746,217 A | 5/1998 | Erickson ..................... 128/760 |
| 5,746,898 A | 5/1998 | Preidel ........................ 204/403 |
| 5,755,733 A | 5/1998 | Morita ........................ 606/182 |
| 5,758,643 A | 6/1998 | Wong et al. ................. 128/632 |
| 5,759,364 A | 6/1998 | Charlton ..................... 204/403 |
| 5,762,770 A | 6/1998 | Pritchard ..................... 204/403 |
| 5,770,086 A | 6/1998 | Indriksons et al. |
| 5,770,369 A | 6/1998 | Meade ........................... 435/6 |
| 5,772,586 A | 6/1998 | Heinonen .................... 600/300 |
| 5,772,677 A | 6/1998 | Mawhirt ..................... 606/181 |
| 5,773,270 A | 6/1998 | D'Orazio ..................... 435/177 |
| 5,776,157 A | 7/1998 | Thorne et al. ............... 606/182 |
| 5,776,719 A | 7/1998 | Douglas ....................... 435/28 |
| 5,779,365 A | 7/1998 | Takaki ........................ 374/161 |
| 5,782,770 A | 7/1998 | Mooradian .................. 600/476 |
| 5,782,852 A | 7/1998 | Foggia ........................ 606/182 |
| 5,788,651 A | 8/1998 | Weilandt .................... 600/567 |
| 5,788,652 A | 8/1998 | Rahn ........................... 600/577 |
| 5,794,219 A | 8/1998 | Brown ........................... 705/37 |
| 5,795,725 A | 8/1998 | Buechler ..................... 435/7.1 |
| 5,795,774 A | 8/1998 | Matsumoto ............... 435/287.9 |
| 5,797,940 A | 8/1998 | Mawhirt ..................... 606/167 |
| 5,797,942 A | 8/1998 | Schraga ....................... 606/182 |
| 5,798,030 A | 8/1998 | Raguse ........................ 204/403 |
| 5,798,031 A | 8/1998 | Charlton ..................... 204/403 |
| 5,800,781 A | 9/1998 | Gavin et al. .................. 422/73 |
| 5,801,057 A | 9/1998 | Smart et al. .................. 436/68 |
| 5,807,375 A | 9/1998 | Gross ......................... 604/890.1 |
| 5,810,199 A | 9/1998 | Charlton et al. ............... 221/31 |
| 5,820,551 A | 10/1998 | Hill ............................ 600/347 |
| 5,822,715 A | 10/1998 | Worthington ................ 702/19 |
| 5,823,973 A | 10/1998 | Racchini et al. ............. 600/573 |
| 5,824,491 A | 10/1998 | Priest .......................... 435/28 |
| 5,828,943 A | 10/1998 | Brown ........................ 434/247 |
| 5,830,219 A * | 11/1998 | Bird et al. ................... 606/130 |
| 5,832,448 A | 11/1998 | Brown ........................... 705/2 |
| 5,840,020 A | 11/1998 | Heinonen ................... 600/309 |
| 5,840,171 A | 11/1998 | Birch ......................... 205/335 |
| 5,846,490 A | 12/1998 | Yokota et al. ................. 422/66 |
| 5,849,174 A | 12/1998 | Sanghera .................... 205/775 |
| 5,853,373 A | 12/1998 | Griffith ....................... 600/554 |
| 5,854,074 A | 12/1998 | Charlton et al. ............. 436/46 |
| D403,975 S | 1/1999 | Douglas ...................... D10/81 |
| 5,855,801 A | 1/1999 | Lin et al. ....................... 216/2 |
| 5,857,983 A | 1/1999 | Douglas ...................... 600/538 |
| 5,860,922 A | 1/1999 | Gordon et al. .............. 600/431 |
| 5,863,800 A | 1/1999 | Eikmeier et al. .............. 436/48 |
| 5,866,353 A | 2/1999 | Berneth ........................ 435/26 |
| 5,868,135 A | 2/1999 | Kaufman .................... 128/630 |
| 5,868,772 A | 2/1999 | LeVaughn ................... 606/181 |
| 5,869,972 A | 2/1999 | Birch ......................... 324/439 |
| 5,871,494 A | 2/1999 | Simons et al. ............... 606/181 |
| 5,872,713 A | 2/1999 | Douglas ....................... 702/85 |
| 5,873,887 A | 2/1999 | King ........................... 606/182 |
| 5,876,957 A | 3/1999 | Douglas ....................... 435/26 |
| 5,879,163 A | 3/1999 | Brown ........................ 434/236 |
| 5,879,310 A | 3/1999 | Sopp ........................... 600/578 |
| 5,879,311 A | 3/1999 | Duchon et al. .............. 600/583 |
| 5,879,373 A | 3/1999 | Roeper ....................... 606/344 |
| 5,880,829 A | 3/1999 | Kauhaniemi et al. ........ 356/246 |
| 5,882,494 A | 3/1999 | van Antwerp ............... 204/403 |
| 5,885,211 A | 3/1999 | Eppstein et al. ............. 600/309 |
| 5,887,133 A | 3/1999 | Brown ...................... 395/200.3 |
| RE36,191 E | 4/1999 | Solomon ..................... 395/308 |
| 5,891,053 A | 4/1999 | Sesekura ..................... 600/583 |
| 5,893,870 A | 4/1999 | Talen ......................... 606/201 |
| 5,897,493 A | 4/1999 | Brown ........................ 600/300 |
| 5,899,855 A | 5/1999 | Brown ........................ 600/301 |
| 5,899,915 A | 5/1999 | Saadat et al. |
| 5,900,130 A | 5/1999 | Benvegnu ................... 204/453 |
| 5,906,921 A | 5/1999 | Ikeda ............................ 435/25 |
| D411,619 S | 6/1999 | Duchon ...................... D24/146 |
| 5,913,310 A | 6/1999 | Brown ........................ 128/897 |
| 5,916,156 A | 6/1999 | Hildenbrand ............... 600/347 |
| 5,916,229 A | 6/1999 | Evans ......................... 606/171 |
| 5,916,230 A | 6/1999 | Brenneman ................. 606/172 |
| 5,918,603 A | 7/1999 | Brown ........................ 128/897 |
| 5,921,963 A | 7/1999 | Erez ........................... 604/192 |
| 5,922,188 A | 7/1999 | Ikeda ........................ 204/777.5 |
| RE36,268 E | 8/1999 | Szuminsky ............... 205/777.5 |
| 5,933,136 A | 8/1999 | Brown ........................ 345/327 |
| 5,935,075 A | 8/1999 | Casscells et al. ............ 600/474 |
| 5,938,679 A | 8/1999 | Freeman et al. ............. 606/181 |
| 5,942,102 A | 8/1999 | Hodges ....................... 205/775 |
| 5,951,300 A | 9/1999 | Brown ........................ 434/236 |
| 5,951,492 A | 9/1999 | Douglas ...................... 600/583 |
| 5,951,493 A | 9/1999 | Douglas et al. .............. 600/583 |
| 5,951,582 A | 9/1999 | Thorne et al. ............... 606/182 |
| 5,951,836 A | 9/1999 | McAleer ..................... 204/403 |
| 5,954,738 A | 9/1999 | LeVaughn ................... 606/181 |
| 5,956,501 A | 9/1999 | Brown ................... 395/500.32 |
| 5,958,199 A | 9/1999 | Miyamoto ................... 204/403 |
| 5,960,403 A | 9/1999 | Brown ........................... 705/2 |
| 5,964,718 A | 10/1999 | Duchon ....................... 600/583 |
| 5,965,380 A | 10/1999 | Heller .......................... 435/14 |
| 5,968,063 A | 10/1999 | Chu et al. .................... 606/185 |
| 5,971,941 A | 10/1999 | Simons et al. .............. 600/573 |
| 5,972,199 A | 10/1999 | Heller ....................... 205/777.5 |
| 5,972,715 A | 10/1999 | Celentano ................... 436/164 |
| 5,974,124 A | 10/1999 | Schlueter ................. 379/106.02 |
| 5,983,193 A | 11/1999 | Heinonen ........................ 705/2 |
| 5,985,116 A | 11/1999 | Ikeda ......................... 204/403 |
| 5,985,559 A | 11/1999 | Brown ............................ 435/6 |
| 5,993,400 A | 11/1999 | Rincoe ....................... 600/595 |
| 5,997,476 A | 12/1999 | Brown ........................ 600/300 |
| 5,997,561 A | 12/1999 | Böcker et al. ............... 606/182 |
| 5,997,817 A | 12/1999 | Crismore ...................... 422/58 |
| 5,997,818 A | 12/1999 | Hackner ..................... 422/681 |
| 6,001,067 A | 12/1999 | Shults ......................... 600/584 |
| 6,007,497 A * | 12/1999 | Huitema ..................... 600/567 |
| 6,015,392 A | 1/2000 | Douglas ...................... 600/583 |
| 6,020,110 A | 2/2000 | Williams ..................... 430/315 |
| 6,022,324 A | 2/2000 | Skinner ....................... 600/566 |
| 6,022,366 A | 2/2000 | Schraga ...................... 606/181 |
| 6,023,686 A | 2/2000 | Brown ......................... 705/37 |
| 6,027,459 A | 2/2000 | Shain et al. ................. 600/573 |
| 6,030,399 A | 2/2000 | Ignotz ......................... 606/167 |
| 6,030,827 A | 2/2000 | Davis .......................... 435/287 |
| 6,032,119 A | 2/2000 | Brown ........................... 705/2 |
| 6,033,421 A | 3/2000 | Theiss ........................ 606/186 |
| 6,033,866 A | 3/2000 | Guo ............................. 435/14 |
| 6,036,924 A | 3/2000 | Simons et al. ............... 422/100 |
| 6,041,253 A | 3/2000 | Kost ............................. 604/20 |
| 6,048,352 A | 4/2000 | Douglas et al. .............. 606/181 |
| D424,696 S | 5/2000 | Ray ............................ D24/169 |
| 6,056,701 A | 5/2000 | Duchon ....................... 600/583 |
| 6,060,327 A | 5/2000 | Keen ........................... 436/518 |
| 6,061,128 A | 5/2000 | Zweig ....................... 356/243.4 |
| 6,063,039 A | 5/2000 | Cunningham ............... 600/573 |
| 6,066,103 A | 5/2000 | Duchon ....................... 600/583 |
| 6,066,296 A | 5/2000 | Brady ........................... 422/63 |
| 6,067,463 A | 5/2000 | Jeng ............................ 600/336 |
| 6,068,615 A | 5/2000 | Brown ......................... 604/207 |
| D426,638 S | 6/2000 | Ray ............................ D24/169 |
| 6,071,249 A | 6/2000 | Cunningham ............... 600/578 |
| 6,071,250 A | 6/2000 | Douglas ...................... 600/583 |

| | | | | | | | |
|---|---|---|---|---|---|---|---|
| 6,071,251 | A | 6/2000 | Cunningham et al. | 6,246,992 | B1 | 6/2001 | Brown .......................... 705/2 |
| 6,071,294 | A | 6/2000 | Simons et al. .............. 606/181 | 6,248,065 | B1 | 6/2001 | Brown ........................ 600/300 |
| 6,074,360 | A | 6/2000 | Haar ........................ 604/57 | 6,251,260 | B1 | 6/2001 | Heller ...................... 205/777.5 |
| 6,077,408 | A | 6/2000 | Miyamoto .................. 204/403 | 6,254,831 | B1 | 7/2001 | Barnard ...................... 422/82.08 |
| 6,080,172 | A | 6/2000 | Fujiwara .................. 606/166 | 6,256,533 | B1 | 7/2001 | Vuzhakov .................... 604/21 |
| 6,083,710 | A | 7/2000 | Heller ........................ 435/14 | 6,258,229 | B1 | 7/2001 | Winarta ...................... 204/403 |
| 6,086,545 | A | 7/2000 | Roe ............................ 600/570 | 6,258,254 | B1 | 7/2001 | Miyamoto ................ 205/777.5 |
| 6,086,562 | A | 7/2000 | Jacobsen ...................... 604/156 | 6,261,241 | B1 | 7/2001 | Burbank et al. ............. 600/564 |
| 6,090,078 | A | 7/2000 | Erskine ...................... 604/198 | 6,261,245 | B1 | 7/2001 | Kawai et al. ................ 600/576 |
| 6,093,146 | A | 7/2000 | Filangeri ...................... 600/300 | 6,261,519 | B1 | 7/2001 | Harding |
| 6,093,156 | A * | 7/2000 | Cunningham et al. ....... 600/573 | 6,268,161 | B1 | 7/2001 | Han .......................... 435/14 |
| 6,101,478 | A | 8/2000 | Brown .......................... 705/2 | 6,270,455 | B1 | 8/2001 | Brown ........................ 600/300 |
| 6,103,033 | A | 8/2000 | Say ............................ 156/73.1 | 6,270,637 | B1 | 8/2001 | Crismore .................... 204/403 |
| 6,107,083 | A | 8/2000 | Collins ...................... 435/288 | 6,272,359 | B1 | 8/2001 | Kivela ........................ 455/567 |
| 6,113,578 | A | 9/2000 | Brown ........................ 604/207 | 6,281,006 | B1 | 8/2001 | Heller ...................... 435/287.9 |
| 6,117,630 | A | 9/2000 | Reber et al. .................... 435/4 | 6,283,926 | B1 | 9/2001 | Cunningham et al. ....... 600/573 |
| 6,120,462 | A | 9/2000 | Hibner et al. ................ 600/566 | 6,283,982 | B1 | 9/2001 | Levaughn .................... 606/172 |
| 6,120,676 | A | 9/2000 | Heller ...................... 205/777.5 | 6,284,478 | B1 | 9/2001 | Heller ........................ 435/14 |
| 6,121,009 | A | 9/2000 | Heller ........................ 435/14 | 6,285,448 | B1 | 9/2001 | Kuenstner .................... 356/39 |
| 6,122,536 | A | 9/2000 | Sun ............................ 600/341 | 6,285,454 | B1 | 9/2001 | Douglas et al. .............. 356/446 |
| 6,129,823 | A | 10/2000 | Hughes .................. 204/403.01 | 6,290,683 | B1 | 9/2001 | Erez .......................... 604/273 |
| 6,132,449 | A | 10/2000 | Lum et al. .................. 606/181 | 6,294,897 | B1 | 9/2001 | Champlin .................... 320/153 |
| 6,133,837 | A | 10/2000 | Riley ........................ 340/573.1 | 6,295,506 | B1 | 9/2001 | Heinonen .................... 702/104 |
| 6,134,461 | A | 10/2000 | Say ............................ 600/345 | 6,299,757 | B1 | 10/2001 | Feldman .................... 205/775 |
| 6,136,013 | A | 10/2000 | Marshall et al. ............. 606/167 | 6,302,844 | B1 | 10/2001 | Walker ........................ 600/300 |
| 6,139,562 | A | 10/2000 | Mauze et al. ................ 606/171 | 6,302,855 | B1 | 10/2001 | Lav .......................... 600/584 |
| 6,143,164 | A | 11/2000 | Heller et al. .............. 205/777.5 | 6,305,804 | B1 | 10/2001 | Rice .......................... 351/221 |
| 6,144,837 | A | 11/2000 | Quy ........................ 434/307 R | 6,306,104 | B1 | 10/2001 | Cunningham et al. ....... 600/573 |
| 6,151,586 | A | 11/2000 | Brown .......................... 705/14 | 6,306,152 | B1 | 10/2001 | Verdonk et al. .............. 606/182 |
| 6,152,875 | A | 11/2000 | Hakamata .................... 600/319 | 6,306,347 | B1 | 10/2001 | Mason ........................ 422/58 |
| 6,152,942 | A | 11/2000 | Brenneman et al. ......... 606/181 | 6,309,535 | B1 | 10/2001 | Williams .................. 205/777.5 |
| 6,153,069 | A | 11/2000 | Pottgen ...................... 204/403 | 6,312,612 | B1 | 11/2001 | Sherman .................... 216/2 |
| RE36,991 | E | 12/2000 | Yamamoto .................. 204/403 | 6,315,738 | B1 * | 11/2001 | Nishikawa et al. .......... 600/583 |
| 6,155,267 | A | 12/2000 | Nelson ...................... 128/899 | 6,319,210 | B1 | 11/2001 | Douglas et al. .............. 600/583 |
| 6,155,992 | A | 12/2000 | Henning et al. .............. 600/583 | 6,322,574 | B1 | 11/2001 | Lloyd .......................... 606/181 |
| 6,156,051 | A | 12/2000 | Schraga ...................... 606/181 | 6,329,161 | B1 | 12/2001 | Heller ........................ 435/14 |
| 6,157,442 | A | 12/2000 | Raskas ........................ 356/39 | 6,330,426 | B2 | 12/2001 | Brown ........................ 434/307 R |
| 6,159,424 | A | 12/2000 | Kauhaniemi et al. ......... 422/63 | 6,331,163 | B1 | 12/2001 | Kaplan ........................ 600/486 |
| 6,161,095 | A | 12/2000 | Brown .......................... 705/2 | 6,332,871 | B1 | 12/2001 | Douglas et al. .............. 600/583 |
| 6,162,611 | A | 12/2000 | Heller ........................ 435/14 | 6,334,363 | B1 | 1/2002 | Testud ........................ 73/862 |
| 6,167,362 | A | 12/2000 | Brown ........................ 703/11 | 6,334,778 | B1 | 1/2002 | Brown ........................ 434/258 |
| 6,167,386 | A | 12/2000 | Brown ........................ 705/37 | 6,334,856 | B1 | 1/2002 | Allen .......................... 604/191 |
| 6,168,563 | B1 | 1/2001 | Brown ........................ 600/301 | 6,338,790 | B1 | 1/2002 | Feldman .................... 205/777.5 |
| 6,171,325 | B1 | 1/2001 | Mauze et al. ................ 356/446 | 6,349,229 | B1 | 2/2002 | Watanabe .................... 600/345 |
| 6,175,752 | B1 | 1/2001 | Say ............................ 600/345 | 6,350,273 | B1 | 2/2002 | Minagawa .................... 606/186 |
| 6,176,865 | B1 | 1/2001 | Mauze et al. ................ 606/171 | 6,350,451 | B1 | 2/2002 | Horn .......................... 424/184.1 |
| 6,177,000 | B1 | 1/2001 | Peterson .................. 205/777.5 | 6,352,514 | B1 | 3/2002 | Douglas et al. .............. 600/583 |
| 6,177,931 | B1 | 1/2001 | Alexander et al. | 6,352,523 | B1 | 3/2002 | Brown ........................ 604/207 |
| 6,183,489 | B1 | 2/2001 | Douglas et al. .............. 606/181 | 6,353,753 | B1 | 3/2002 | Flock .......................... 600/473 |
| 6,186,145 | B1 | 2/2001 | Brown ........................ 128/897 | 6,364,889 | B1 | 4/2002 | Kheiri et al. ................ 606/181 |
| 6,190,612 | B1 | 2/2001 | Berger ........................ 422/82.07 | 6,364,890 | B1 | 4/2002 | Lum et al. .................... 606/181 |
| 6,191,852 | B1 | 2/2001 | Paffhausen .................. 356/244 | 6,368,273 | B1 | 4/2002 | Brown ........................ 600/300 |
| 6,192,891 | B1 | 2/2001 | Gravel ........................ 128/920 | 6,375,469 | B1 | 4/2002 | Brown ........................ 434/236 |
| 6,193,673 | B1 | 2/2001 | Viola et al. .................. 600/568 | 6,375,627 | B1 | 4/2002 | Mauze et al. ................ 600/584 |
| 6,194,900 | B1 | 2/2001 | Freeman .................... 324/321 | 6,379,301 | B1 | 4/2002 | Worthington ................ 600/309 |
| 6,197,257 | B1 | 3/2001 | Raskas .................... 422/82.05 | 6,379,317 | B1 | 4/2002 | Kintzig et al. ................ 600/573 |
| 6,203,504 | B1 | 3/2001 | Latterell et al. .............. 600/576 | 6,379,324 | B1 | 4/2002 | Gartstein .................... 604/22 |
| 6,206,841 | B1 | 3/2001 | Cunningham et al. ....... 600/584 | 6,379,969 | B1 | 4/2002 | Mauze et al. ................ 436/68 |
| 6,210,272 | B1 | 4/2001 | Brown .......................... 463/1 | 6,381,577 | B1 | 4/2002 | Brown .......................... 705/2 |
| 6,210,420 | B1 | 4/2001 | Mauze et al. ................ 606/182 | 6,387,709 | B1 | 5/2002 | Mason ........................ 436/164 |
| 6,210,421 | B1 | 4/2001 | Böcker et al. .............. 606/182 | 6,391,005 | B1 | 5/2002 | Lum et al. .................... 604/117 |
| 6,212,417 | B1 | 4/2001 | Ikeda .................... 204/403.14 | 6,399,394 | B1 | 6/2002 | Dahm ........................ 436/180 |
| 6,214,804 | B1 | 4/2001 | Felgner ........................ 514/44 | 6,402,701 | B1 | 6/2002 | Kaplan et al. ................ 600/567 |
| 6,221,238 | B1 | 4/2001 | Grundig .................... 205/777.5 | 6,402,704 | B1 | 6/2002 | McMorrow .................. 600/576 |
| 6,225,078 | B1 | 5/2001 | Ikeda .......................... 435/25 | 6,409,740 | B1 | 6/2002 | Kuhr et al. .................. 606/182 |
| 6,228,100 | B1 | 5/2001 | Schraga ...................... 606/183 | 6,413,410 | B1 | 7/2002 | Hodges ...................... 205/775 |
| 6,230,501 | B1 | 5/2001 | Bailey ........................ 62/51.1 | 6,413,411 | B1 | 7/2002 | Pottgen .................... 205/777.5 |
| 6,231,531 | B1 | 5/2001 | Lum et al. .................... 601/46 | 6,421,633 | B1 | 7/2002 | Heinonen .................... 703/11 |
| 6,233,471 | B1 | 5/2001 | Berner ........................ 600/345 | 6,423,014 | B1 | 7/2002 | Churchill et al. |
| 6,233,539 | B1 | 5/2001 | Brown ........................ 703/11 | 6,428,664 | B1 | 8/2002 | Bhullar .................... 204/403.03 |
| 6,240,393 | B1 | 5/2001 | Brown .......................... 705/1 | 6,436,256 | B1 | 8/2002 | Williams .................. 204/403.06 |
| 6,241,862 | B1 | 6/2001 | McAleer .................... 204/403 | 6,436,721 | B1 | 8/2002 | Kuo .......................... 436/514 |
| 6,245,060 | B1 | 6/2001 | Loomis ........................ 606/9 | 6,440,645 | B1 | 8/2002 | Yon-Hin ...................... 430/322 |

| | | | |
|---|---|---|---|
| 6,451,040 B1 | 9/2002 | Purcell | 606/181 |
| 6,458,258 B2 | 10/2002 | Taniike | 204/403 |
| 6,461,496 B1 | 10/2002 | Feldman et al. | 205/777.5 |
| 6,462,162 B2 | 10/2002 | van Antwerp | 528/77 |
| 6,464,649 B1 | 10/2002 | Duchon | 600/583 |
| 6,471,903 B2 | 10/2002 | Sherman | 264/328.1 |
| 6,472,220 B1 | 10/2002 | Simons et al. | 436/63 |
| 6,475,436 B1 | 11/2002 | Schabbach | 422/64 |
| 6,475,750 B1 | 11/2002 | Han | 435/14 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,485,439 B1 | 11/2002 | Roe et al. | 600/578 |
| 6,488,891 B2 | 12/2002 | Mason et al. | 422/58 |
| 6,489,052 B1 | 12/2002 | Acker | 600/584 |
| 6,491,709 B2 | 12/2002 | Sharma et al. | 606/181 |
| 6,494,830 B1 | 12/2002 | Wessel | 600/300 |
| 6,497,845 B1 | 12/2002 | Sacherer | 422/104 |
| 6,501,404 B2 | 12/2002 | Walker | 341/143 |
| 6,503,210 B1 | 1/2003 | Hirao et al. | 600/576 |
| 6,503,231 B1 | 1/2003 | Praunsnitz | 604/272 |
| 6,503,381 B1 | 1/2003 | Gotoh | 204/403.14 |
| 6,506,168 B1 | 1/2003 | Fathallah | 600/578 |
| 6,506,575 B1 | 1/2003 | Knappe et al. | 435/25 |
| 6,508,785 B1 | 1/2003 | Eppstein | 604/113 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,527,778 B2 | 3/2003 | Athanasiou | 606/80 |
| 6,530,892 B1 | 3/2003 | Kelly | 600/583 |
| 6,530,937 B1 | 3/2003 | Schraga | 606/182 |
| 6,533,949 B1 | 3/2003 | Yeshurun | 216/11 |
| 6,537,207 B1 | 3/2003 | Rice | 600/121 |
| 6,537,242 B1 | 3/2003 | Palmer | 604/22 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,541,266 B2 | 4/2003 | Modzelewski | 436/95 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller | 205/777.5 |
| 6,553,244 B2 | 4/2003 | Lesho | 600/347 |
| 6,554,381 B2 | 4/2003 | Locher | 347/7 |
| 6,555,061 B1 | 4/2003 | Leong | 422/58 |
| 6,558,320 B1 | 5/2003 | Causey | 600/300 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,560,471 B1 | 5/2003 | Heller | 600/347 |
| 6,561,978 B1 | 5/2003 | Conn | 600/309 |
| 6,561,989 B2 | 5/2003 | Whitson | 600/573 |
| 6,562,210 B1 | 5/2003 | Bhullar | 204/403.3 |
| 6,565,509 B1 | 5/2003 | Say | 600/365 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,574,490 B2 | 6/2003 | Abbink | 600/316 |
| 6,575,905 B2 | 6/2003 | Knobbe | 600/365 |
| 6,576,101 B1 | 6/2003 | Heller | 204/403.14 |
| 6,576,117 B1 | 6/2003 | Iketaki | 205/777.5 |
| 6,576,416 B2 | 6/2003 | Haviland | 435/4 |
| 6,582,573 B2 | 6/2003 | Douglas | 204/403.1 |
| 6,587,705 B1 | 7/2003 | Kim | 600/347 |
| 6,589,260 B1 | 7/2003 | Schmelzeisen | 606/181 |
| 6,589,261 B1 | 7/2003 | Abulhaj | 606/181 |
| 6,591,125 B1 | 7/2003 | Buse | 600/347 |
| 6,592,745 B1 | 7/2003 | Feldman | 205/777.5 |
| 6,595,919 B2 | 7/2003 | Berner | 600/365 |
| 6,599,407 B2 | 7/2003 | Taniike | 204/403.1 |
| 6,599,693 B1 | 7/2003 | Webb | 435/4 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,604,050 B2 | 8/2003 | Trippel | 702/19 |
| 6,607,494 B1 | 8/2003 | Fowler | 600/570 |
| 6,607,658 B1 | 8/2003 | Heller | 205/777.5 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,623,501 B2 | 9/2003 | Heller | 606/181 |
| 6,626,851 B2 | 9/2003 | Hirao | 600/576 |
| 6,635,222 B2 | 10/2003 | Kent | 422/22 |
| 6,638,772 B1 | 10/2003 | Douglas | 436/518 |
| 6,641,533 B2 | 11/2003 | Causey | 600/300 |
| 6,645,142 B2 | 11/2003 | Braig | 600/300 |
| 6,645,219 B2 | 11/2003 | Roe | 606/182 |
| 6,645,368 B1 | 11/2003 | Beatty | 205/792 |
| 6,650,915 B2 | 11/2003 | Routt | 600/319 |
| 6,652,720 B1 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Peterson | 600/316 |
| 6,679,841 B2 | 1/2004 | Bojan | 600/309 |
| 6,679,852 B1 | 1/2004 | Schmelzeisen-Redeker | 600/583 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,713,660 B1 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 606/9 |
| 6,736,777 B2 | 5/2004 | Kim | 600/365 |
| 6,740,215 B1 | 5/2004 | Nakaminami | 204/403.14 |
| 6,743,211 B1 | 6/2004 | Prausnitz | 604/239 |
| 6,743,635 B2 | 6/2004 | Neel | 436/95 |
| 6,749,618 B2 | 6/2004 | Levaughn | 606/182 |
| 6,749,792 B2 | 6/2004 | Olsen | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |

| Patent | Date | Name | Ref |
|---|---|---|---|
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,406 B2 | 11/2004 | Grubge | |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 5,059,789 A1 | 1/2005 | Goldman | 435/4 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/452 |
| 6,843,254 B2 | 1/2005 | Tapper | 128/898 |
| 6,847,451 B2 | 1/2005 | Pugh | 356/436 |
| 6,849,052 B2 | 2/2005 | Uchigaki et al. | |
| 6,849,168 B2 | 2/2005 | Crumly | 204/416 |
| 6,849,216 B2 | 2/2005 | Rappin | 264/134 |
| 6,850,790 B2 | 2/2005 | Berner | 600/347 |
| 6,869,418 B2 | 3/2005 | Marano-Ford | 604/192 |
| 6,872,200 B2 | 3/2005 | Mann | 604/890.1 |
| 6,875,208 B2 | 4/2005 | Santini | 604/890.1 |
| 6,875,223 B2 | 4/2005 | Argauer | 606/181 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/403 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,541 B2 | 4/2005 | Petersen et al. | |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 6,887,239 B2 | 5/2005 | Elstrom | 606/41 |
| 6,887,253 B2 | 5/2005 | Schraga | 606/181 |
| 6,887,254 B1 | 5/2005 | Curie | 606/181 |
| 6,887,426 B2 | 5/2005 | Phillips | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russel | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,916,410 B2 | 7/2005 | Katsuki | 204/403 |
| 6,918,874 B1 | 7/2005 | Hatch | 600/365 |
| 6,918,901 B1 | 7/2005 | Theeuwes et al. | |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,964,871 B2 | 11/2005 | Bell | 436/95 |
| 6,965,791 B2 | 11/2005 | Hitchcock | 600/345 |
| 6,966,880 B2 | 11/2005 | Boecker | 600/583 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |

| Patent | Date | Name | Class |
|---|---|---|---|
| 6,975,893 B2 | 12/2005 | Say | 600/347 |
| 6,977,032 B2 | 12/2005 | Hasegawa | 204/403.05 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin et al. | |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 * | 2/2006 | Freeman et al. | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,044,911 B2 | 5/2006 | Drinan | 600/300 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,060,059 B2 | 6/2006 | Keith | 604/504 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Jeong | 606/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |

| Patent/Pub No. | Date | Name | Class |
|---|---|---|---|
| 7,138,089 B2 | 11/2006 | Aitken | 422/82.01 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorezyk | 205/792 |
| 7,144,496 B2 | 12/2006 | Meserol | 205/792 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,160,251 B2 | 1/2007 | Neel | 600/365 |
| 7,160,313 B2 | 1/2007 | Galloway | 606/167 |
| 7,160,678 B1 | 1/2007 | Kayyem et al. | |
| 7,163,616 B2 | 1/2007 | Vreeke | 205/777.5 |
| 7,166,074 B2 | 1/2007 | Reghabi | 600/365 |
| 7,167,734 B2 | 1/2007 | Khalil | 600/310 |
| 7,167,818 B2 | 1/2007 | Brown | 703/11 |
| 7,225,535 B2 | 6/2007 | Feldman et al. | |
| 7,226,461 B2 | 6/2007 | Boecker et al. | |
| 2001/0011157 A1 | 8/2001 | Latterell | 600/576 |
| 2001/0016682 A1 | 8/2001 | Berner | 600/573 |
| 2001/0017269 A1 | 8/2001 | Heller | 205/777.5 |
| 2001/0027328 A1 | 10/2001 | Lum | 606/186 |
| 2001/0031931 A1 | 10/2001 | Cunningham et al. | 600/573 |
| 2001/0054319 A1 | 12/2001 | Heller | 73/849 |
| 2002/0002344 A1 | 1/2002 | Douglas et al. | 600/583 |
| 2002/0004196 A1 | 1/2002 | Whitson | 435/4 |
| 2002/0016606 A1 | 2/2002 | Moerman | 606/181 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum et al. | |
| 2002/0044890 A1 | 4/2002 | Black | 422/56 |
| 2002/0052618 A1 | 5/2002 | Haar et al. | 606/181 |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0082543 A1 | 6/2002 | Park et al. | 604/21 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0103499 A1 | 8/2002 | Perez et al. | 606/182 |
| 2002/0120216 A1 | 8/2002 | Fritz | 600/583 |
| 2002/0120261 A1 | 8/2002 | Morris | 606/41 |
| 2002/0130042 A1 | 9/2002 | Moerman et al. | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0176984 A1 | 11/2002 | Smart | 428/336 |
| 2002/0177761 A1 | 11/2002 | Orloff | 600/309 |
| 2002/0188224 A1 | 12/2002 | Roe | 600/584 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0060730 A1 | 3/2003 | Perez | 600/576 |
| 2003/0069753 A1 | 4/2003 | Brown | 705/2 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman et al. | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0135333 A1 | 7/2003 | Aceti | 702/31 |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149393 A1 | 8/2003 | Erickson | 600/573 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | Yuzhakov | 600/584 |
| 2003/0212347 A1 | 11/2003 | Sohrab | 600/584 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |

| Pub. No. | Date | Inventor | Class |
|---|---|---|---|
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0030353 A1 | 2/2004 | Schmelzeisen | 606/181 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 600/316 |
| 2004/0055898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0087990 A1 | 5/2004 | Boecker | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107116 A1 | 6/2004 | Brown | 705/2 |
| 2004/0115754 A1 | 6/2004 | Chang | 435/14 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Mauze | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0199409 A1 | 10/2004 | Brown | 705/3 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219500 A1 | 11/2004 | Brown | 434/307 R |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220564 A1 | 11/2004 | Ho | 606/47 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |
| 2004/0238358 A1 | 12/2004 | Forrow | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |

| Pub. No. | Date | Name | Ref. |
|---|---|---|---|
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/181 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode et al. | |
| 2005/0027211 A1 | 2/2005 | Kuhr | 600/583 |
| 2005/0027562 A1 | 2/2005 | Brown | 705/2 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Nakahara | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0059895 A1 | 3/2005 | Brown | 600/481 |
| 2005/0060194 A1 | 3/2005 | Brown | 705/2 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Gundel | 204/403.2 |
| 2005/0098433 A1 | 5/2005 | Gundel | 204/403.2 |
| 2005/0098434 A1 | 5/2005 | Gundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137536 A1 | 6/2005 | Gonnelli | 604/173 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |

| Pub. No. | Date | Inventor | Class |
|---|---|---|---|
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Saito et al. | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030788 A1 | 2/2006 | Wong | 600/583 |
| 2006/0034728 A1 | 2/2006 | Kloepfer | 422/68.1 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094986 A1 | 5/2006 | Neel | 600/583 |
| 2006/0095061 A1 | 5/2006 | Trautman | 606/185 |

| Pub. No. | Date | Inventor | Class |
|---|---|---|---|
| 2006/0096859 A1 | 5/2006 | King Tong Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0151342 A1 | 7/2006 | Yaguchi | 206/306 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0161078 A1 | 7/2006 | Schraga | 600/583 |
| 2006/0161194 A1 | 7/2006 | Freeman | 606/185 |
| 2006/0166302 A1 | 7/2006 | Clarke | 435/25 |
| 2006/0167382 A1 | 7/2006 | Deshmukh | 600/583 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231442 A1 | 10/2006 | Windus-Smith | 206/438 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |
| 2007/0004990 A1 | 1/2007 | Kistner | 600/583 |
| 2007/0007183 A1 | 1/2007 | Schulat | 209/573 |
| 2007/0009381 A1 | 1/2007 | Schulat | 422/58 |
| 2007/0010839 A1 | 1/2007 | Galloway | 606/167 |
| 2007/0010841 A1 | 1/2007 | Teo | 606/181 |
| 2007/0015978 A1 | 1/2007 | Kanayama | 600/310 |
| 2007/0016079 A1 | 1/2007 | Freeman | 600/476 |
| 2007/0016103 A1 | 1/2007 | Calasso | 600/583 |
| 2007/0016104 A1 | 1/2007 | Jansen | 600/583 |

FOREIGN PATENT DOCUMENTS

| | | |
|---|---|---|
| DE | 29824204 | 10/2000 |
| DE | 10032042 | 1/2002 |
| DE | 10057832 | 2/2002 |
| DE | 10057832 C1 | 2/2002 |
| DE | 10142232 | 3/2003 |
| DE | 10208575 C1 | 8/2003 |
| DE | 10245721 | 12/2003 |
| DE | 10361560 A1 | 7/2005 |
| EP | 0199484 A2 | 10/1986 |
| EP | 0289 269 | 11/1988 |
| EP | 0320109 | 6/1989 |
| EP | 0 364 208 A1 | 4/1990 |
| EP | 0170375 | 5/1990 |
| EP | 0136362 | 12/1990 |

| | | | | | | |
|---|---|---|---|---|---|---|
| EP | 0453283 | 10/1991 | | WO | WO 94/29731 | 12/1994 |
| EP | 0263948 | 2/1992 | | WO | WO 95/00662 | 1/1995 |
| EP | 0374355 | 6/1993 | | WO | WO 95/06240 | 3/1995 |
| EP | 0351891 | 9/1993 | | WO | WO 95/10223 | 4/1995 |
| EP | 0593096 | 4/1994 | | WO | WO 95/22597 | 8/1995 |
| EP | 0415388 | 5/1995 | | WO | WO 96/30431 | 10/1996 |
| EP | 0505494 | 7/1995 | | WO | WO 97/02359 | 1/1997 |
| EP | 0359831 | 8/1995 | | WO | WO 97/02487 | 1/1997 |
| EP | 0471986 | 10/1995 | | WO | WO 97/18464 | 5/1997 |
| EP | 0368474 | 12/1995 | | WO | WO 97/30344 | 8/1997 |
| EP | 0461601 | 12/1995 | | WO | WO 97/42882 | 11/1997 |
| EP | 0429076 | 1/1996 | | WO | WO 97/42888 | 11/1997 |
| EP | 0552223 | 7/1996 | | WO | WO 97/45720 | 12/1997 |
| EP | 0735363 | 10/1996 | | WO | WO 98/03431 | 1/1998 |
| EP | 0505504 | 3/1997 | | WO | WO 98/19159 | 5/1998 |
| EP | 0406304 | 8/1997 | | WO | WO 98/20332 | 5/1998 |
| EP | 0537761 | 8/1997 | | WO | WO 98/20348 | 5/1998 |
| EP | 0795601 | 9/1997 | | WO | WO 98/24366 | 6/1998 |
| EP | 0562370 | 11/1997 | | WO | WO 98/24373 | 6/1998 |
| EP | 0415393 | 12/1997 | | WO | WO 98/35225 | 8/1998 |
| EP | 0560336 | 5/1998 | | WO | WO 99/03584 | 1/1999 |
| EP | 0878 708 | 11/1998 | | WO | WO 99/05966 | 2/1999 |
| EP | 0 898 936 A2 | 3/1999 | | WO | WO 99/07431 A1 | 2/1999 |
| EP | 0505475 | 3/1999 | | WO | WO 99/13100 | 3/1999 |
| EP | 0901018 | 3/1999 | | WO | WO 99/17854 | 4/1999 |
| EP | 0470649 | 6/1999 | | WO | WO 99/18532 | 4/1999 |
| EP | 0 951 939 | 10/1999 | | WO | WO 99/19507 | 4/1999 |
| EP | 0 951 939 A2 | 10/1999 | | WO | WO 99/19717 | 4/1999 |
| EP | 0847447 | 11/1999 | | WO | WO 99/27483 | 6/1999 |
| EP | 0964059 | 12/1999 | | WO | WO 99/27852 | 6/1999 |
| EP | 0969097 | 1/2000 | | WO | WO 99/62576 | 12/1999 |
| EP | 0 985 376 | 5/2000 | | WO | WO 99/64580 | 12/1999 |
| EP | 1021950 | 7/2000 | | WO | WO 00/06024 | 2/2000 |
| EP | 0894869 | 2/2001 | | WO | WO 00/09184 | 2/2000 |
| EP | 1074832 | 2/2001 | | WO | WO 00/11578 | 3/2000 |
| EP | 1093854 | 4/2001 | | WO | WO 00/15103 | 3/2000 |
| EP | 1 101 443 | 5/2001 | | WO | WO 00/17799 | 3/2000 |
| EP | 1101443 | 5/2001 | | WO | WO 00/17800 | 3/2000 |
| EP | 1114995 | 7/2001 | | WO | WO 00/18293 | 4/2000 |
| EP | 0736607 | 8/2001 | | WO | WO 00/19346 | 4/2000 |
| EP | 0874984 | 11/2001 | | WO | WO 00/30186 | 5/2000 |
| EP | 0730037 | 12/2001 | | WO | WO 00/32097 | 6/2000 |
| EP | 0636879 | 1/2002 | | WO | WO 00/32098 | 6/2000 |
| EP | 01174083 | 1/2002 | | WO | WO 00/33236 | 6/2000 |
| EP | 0851224 | 3/2002 | | WO | WO 00/39914 | 7/2000 |
| EP | 0759553 | 5/2002 | | WO | WO 00/40150 | 7/2000 |
| EP | 0856586 | 5/2002 | | WO | WO 00/42422 | 7/2000 |
| EP | 0817809 | 7/2002 | | WO | WO 00/44084 | 7/2000 |
| EP | 0872728 | 7/2002 | | WO | WO 00/50771 | 8/2000 |
| EP | 0795748 | 8/2002 | | WO | WO 00/60340 | 10/2000 |
| EP | 0685737 | 9/2002 | | WO | WO 00/64022 | 10/2000 |
| EP | 0958495 | 11/2002 | | WO | WO 00/67245 | 11/2000 |
| EP | 0937249 | 12/2002 | | WO | WO 00/67268 | 11/2000 |
| EP | 0880692 | 1/2004 | | WO | WO 00/72452 | 11/2000 |
| EP | 01374770 | 1/2004 | | WO | WO 01/00090 | 1/2001 |
| EP | 1246688 | 5/2004 | | WO | WO 01/00090 A1 | 1/2001 |
| EP | 1502614 | 2/2005 | | WO | WO 01/15807 | 3/2001 |
| FR | 2 555 432 A | 5/1985 | | WO | WO 01/16578 A1 | 3/2001 |
| GB | 2168815 | 6/1986 | | WO | WO 01/75433 | 3/2001 |
| GB | 233936 A | 6/1999 | | WO | WO 01/23885 | 4/2001 |
| GB | 2335860 A | 10/1999 | | WO | WO 01/25775 | 4/2001 |
| GB | 2335990 A | 10/1999 | | WO | WO 01/26813 | 4/2001 |
| JP | 2-326247 | 11/1990 | | WO | WO 01/33216 | 5/2001 |
| JP | 10-296325 | 10/1998 | | WO | WO 01/34029 | 5/2001 |
| WO | WO 80/01389 | 7/1980 | | WO | WO 01/36955 | 5/2001 |
| WO | WO 85/04089 | 9/1985 | | WO | WO 01/37174 | 5/2001 |
| WO | WO 86/07632 | 12/1986 | | WO | WO 01/45014 A1 | 6/2001 |
| WO | WO 91/09139 | 7/1991 | | WO | WO 01/40788 | 7/2001 |
| WO | WO 93/06979 | 4/1993 | | WO | WO 01/57510 | 8/2001 |
| WO | WO 93/25898 | 12/1993 | | WO | WO 01/64105 | 9/2001 |
| WO | WO 94/27140 | 11/1994 | | WO | WO 01/66010 | 9/2001 |
| WO | WO 94/29703 | 12/1994 | | WO | WO 01/66010 A1 | 9/2001 |
| WO | WO 94/29704 | 12/1994 | | WO | WO 01/69505 | 9/2001 |

| | | |
|---|---|---|
| WO | WO 01/72220 A | 10/2001 |
| WO | WO 01/72225 | 10/2001 |
| WO | WO 01/73124 | 10/2001 |
| WO | WO 01/73395 | 10/2001 |
| WO | WO 01/89691 | 11/2001 |
| WO | WO 02/00101 | 1/2002 |
| WO | WO 02/02796 | 1/2002 |
| WO | WO 02/08750 | 1/2002 |
| WO | WO 02/08753 | 1/2002 |
| WO | WO 02/08950 | 1/2002 |
| WO | WO 02/18940 | 3/2002 |
| WO | WO 02/21317 | 3/2002 |
| WO | WO 02/25551 | 3/2002 |
| WO | WO 02/32559 | 4/2002 |
| WO | WO 02/41227 | 5/2002 |
| WO | WO 02/41779 | 5/2002 |
| WO | WO 02/44948 | 6/2002 |
| WO | WO 02/056769 A1 | 7/2002 |
| WO | WO 02/059734 | 8/2002 |
| WO | WO 02/069791 | 9/2002 |
| WO | WO 02/077638 | 10/2002 |
| WO | WO 02/100251 | 12/2002 |
| WO | WO 02/100252 | 12/2002 |
| WO | WO 02/100253 | 12/2002 |
| WO | WO 02/100254 | 12/2002 |
| WO | WO 02/100460 | 12/2002 |
| WO | WO 02/100461 | 12/2002 |
| WO | WO 02/101343 | 12/2002 |
| WO | WO 02/101359 | 12/2002 |
| WO | WO 03/000321 | 1/2003 |
| WO | WO 03/023389 | 3/2003 |
| WO | WO 03/042691 | 5/2003 |
| WO | WO 03/045557 | 6/2003 |
| WO | WO 03/046542 | 6/2003 |
| WO | WO 03/049609 | 6/2003 |
| WO | WO 03/050534 | 6/2003 |
| WO | WO 03/066128 | 8/2003 |
| WO | WO 03/070099 | 8/2003 |
| WO | WO 03/071940 | 9/2003 |
| WO | WO 03/088851 A1 | 10/2003 |
| WO | WO 03/094752 | 11/2003 |
| WO | WO 03/101297 | 12/2003 |
| WO | WO 2004/008130 | 1/2004 |
| WO | WO 2004/022133 | 3/2004 |
| WO | WO 2004/026130 | 4/2004 |
| WO | WO 2004/040285 A2 | 5/2004 |
| WO | WO 2004/040287 A1 | 5/2004 |
| WO | WO 2004/040948 | 5/2004 |
| WO | WO 2004/041082 | 5/2004 |
| WO | WO 2004/054455 | 7/2004 |
| WO | WO 2004/060174 | 7/2004 |
| WO | WO 2004/060446 | 7/2004 |
| WO | WO 2004/091693 | 10/2004 |
| WO | WO 2004/098405 | 11/2004 |
| WO | WO 2004/003147 | 12/2004 |
| WO | WO 2004/107964 | 12/2004 |
| WO | WO 2004/107975 | 12/2004 |
| WO | WO 2004/112602 | 12/2004 |
| WO | WO 2005/001418 | 1/2005 |
| WO | WO 2005/006939 | 1/2005 |
| WO | WO 2005/011774 | 2/2005 |
| WO | WO 2005/016125 | 2/2005 |
| WO | WO 2005/018425 | 3/2005 |
| WO | WO 2005/018430 | 3/2005 |
| WO | WO 2005/018454 | 3/2005 |
| WO | WO 2005/018709 | 3/2005 |
| WO | WO 2005/018710 | 3/2005 |
| WO | WO 2005/018711 | 3/2005 |
| WO | WO 2005/022143 | 3/2005 |
| WO | WO 2005/023088 | 3/2005 |
| WO | WO 2005/033659 | 4/2005 |
| WO | WO 2005/034720 | 4/2005 |
| WO | WO 2005/034721 | 4/2005 |
| WO | WO 2005/034741 | 4/2005 |
| WO | WO 2005/034778 | 4/2005 |
| WO | WO 2005/035017 | 4/2005 |
| WO | WO 2005/035018 | 4/2005 |
| WO | WO 2005/037095 | 4/2005 |
| WO | WO 2005/046477 | 5/2005 |
| WO | WO 2005/065399 | 7/2005 |
| WO | WO 2005/065414 | 7/2005 |
| WO | WO 2005/065415 | 7/2005 |
| WO | WO 2005/065415 A2 | 7/2005 |
| WO | WO 2005/072604 | 8/2005 |
| WO | WO 2005/084557 | 9/2005 |
| WO | WO 2005/116622 | 12/2005 |
| WO | WO 2005/119234 | 12/2005 |
| WO | WO 2005/121759 | 12/2005 |
| WO | WO 2006/001973 | 1/2006 |
| WO | WO 2006/011062 | 2/2006 |
| WO | WO 2006/013045 | 2/2006 |
| WO | WO 2006/027702 A2 | 3/2006 |
| WO | WO 2006/032391 | 3/2006 |
| WO | WO 2006/072004 | 7/2006 |

OTHER PUBLICATIONS

International Search Report (PCT/ISA/220) for PCT/US02/19054.
International Search Report (PCT/ISA/220) for PCT/US02/19059.
Written Opinion (certain documents cited) for PCT/US02/19059.
International Search Report (PCT/ISA/220) for PCT/US02/19060.
International Search Report (PCT/ISA/220) for PCT/US02/19450.
International Search Report (PCT/ISA/220) for PCT/US02/19057.
International Search Report (PCT/ISA/220) for PCT/US02/19053.
International Search Report (PCT/ISA/220) for PCT/US02/19188.
International Search Report (PCT/ISA/220) for PCT/US03/12555.
International Search Report (PCT/ISA/220) for PCT/US03/12381.
International Search Report (PCT/ISA/220) for PCT/US03/12546.
International Search Report (PCT/ISA/220) for PCT/US03/35015.
International Search Report (PCT/ISA/220) for PCT/US03/40095.
International Search Report (PCT/ISA/220) for PCT/US03/41747.

* cited by examiner

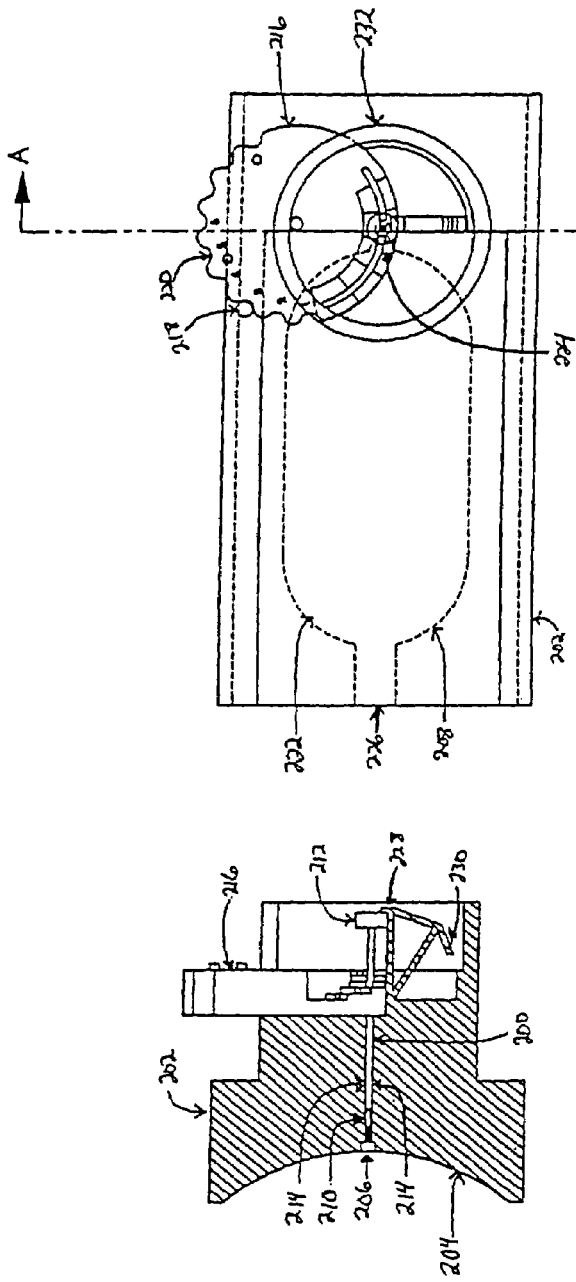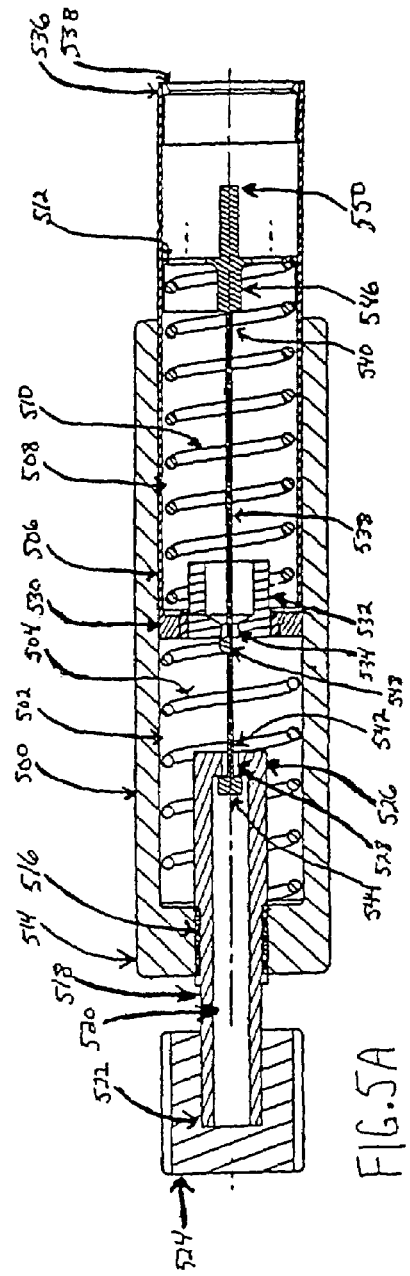

BLOOD SAMPLING APPARATUS AND METHOD

TECHNICAL FIELD

Biochemical analysis of blood samples is an important diagnostic tool for determination of patient status. Analysis of a blood sample for glucose level can provide a powerful tool for diabetics who require tight control of blood glucose levels in an effort to minimize the deleterious long-term effects of the disease. At this time, noninvasive blood analysis technology does not provide the accuracy and specificity required for clinical testing, so that test samples are mainly derived from blood, interstitial fluid, urine or saliva Many point of care tests are performed directly on capillary whole blood, which is typically obtained by making a small incision on a finger using a hand-held lancing device. The hand-held lancing device usually includes a lancet that is rapidly displaced to penetrate the finger, creating a small wound from which a blood droplet forms on the surface of the skin after the lancet has retracted from the incision. Generally the blood droplet is placed on a sample assay strip, and the sample assay strip is analyzed using a measurement device.

BACKGROUND ART

The process of acquiring and testing a blood sample using these conventional devices can be painful and often involves numerous steps, the outcome of which is to reduce patient compliance with the frequent self testing regimens required for disease management. In addition to the pain and the paraphernalia required for self-testing, the success rate of obtaining an adequate blood sample is not 100%. The success rate can be affected by the reproducibility of the lancing technique used (due to variation in skin hydration and thickness, calluses, etc.) as well as the ability to obtain the blood droplet from the incision. Current industry standard lancet and lancing devices can have as low as a 50% success rate in generating a blood sample from the fingertip. The diabetic wishing to adhere to the optimal 5-6 times a day self testing regimen would, in essence, need to lance themselves an average of 10-12 times just to obtain the blood samples required. The more successful lancing devices are, in reality, about 80-90% successful.

What has been needed is an improved method for sampling and analyzing bodily fluid which is seamless and cost-efficient resulting in a simplified procedure for extraction and analysis of blood samples at the patient's side.

DISCLOSURE OF INVENTION

Embodiments of the invention allow acquisition of the blood sample seamlessly, that is, without substantial contamination from ambient air, such that the blood sample may be analyzed accurately for gaseous components such as oxygen and carbon dioxide. Embodiments of the invention have integrated actuation, lancing, and sample acquisition components, which can optionally be miniaturized and/or disposable. Sampled blood can be acquired and transported to an analysis or storage device without substantial contamination by ambient air.

Embodiments of the disposable sample acquisition module can collect a sample in an integrated fashion. In the operation of some embodiments, a finger of the user is placed on the sampling site, where the finger remains throughout the integrated lancing and sample collection process.

In certain embodiments of the invention, in order to facilitate adequate sample volume for analysis, three approaches are described, of which a single approach might be used, or any two or all three approaches may be used in concert. The first approach describes a surface treatment of the support material to engender a difference in wetting ability. The second describes an active pumping device in addition to capillary forces for drawing the blood into the sample reservoir and for dispensing blood from the reservoir to additional sites. The third includes the use of a device which compensates for an inadequate sample volume in the first sample reservoir by isolating the first sample reservoir and triggering a second lancing and acquisition step to fill a second "backup" sample reservoir.

One embodiment of the invention is directed to a miniature lancing and blood sampling device. Analysis of small blood volumes (less than about one milliliter) is achieved by the collection and the transportation of the blood micro sample to sample storage area or analytical sites. Sampled blood can be transported reliably and without excessive turbulence, cavitation or damage to the cellular components. Furthermore, analyte detection is achieved via the blood samples reliably reaching and saturating the appropriate test sites. Embodiments of the invention provide techniques for extracting a sample of human blood for the measurement of one or more of its constituents, such as might be used for routine monitoring of a chronic condition such as diabetes mellitus. The techniques of embodiments of the present invention simplify the extraction and transfer of the blood sample, and reduce the inconvenience of the process. The techniques can be advantageously used in, for example, blood glucose monitoring as explained above.

BRIEF DESCRIPTION OF DRAWING

The objects, advantages and features of this invention will be more readily appreciated from the following detailed description, when read in conjunction with the accompanying drawing, in which:

FIG. 2A is a cross section view through line A of FIG. 2B, which shows some details of a sample acquisition module according to embodiments of the invention.

FIGS. 5A, 5B, and 5C show in section view one implementation of the lancet driver at three different points during the use of the lancet driver.

BEST MODE FOR CARRYING OUT THE INVENTION

Figure 1:
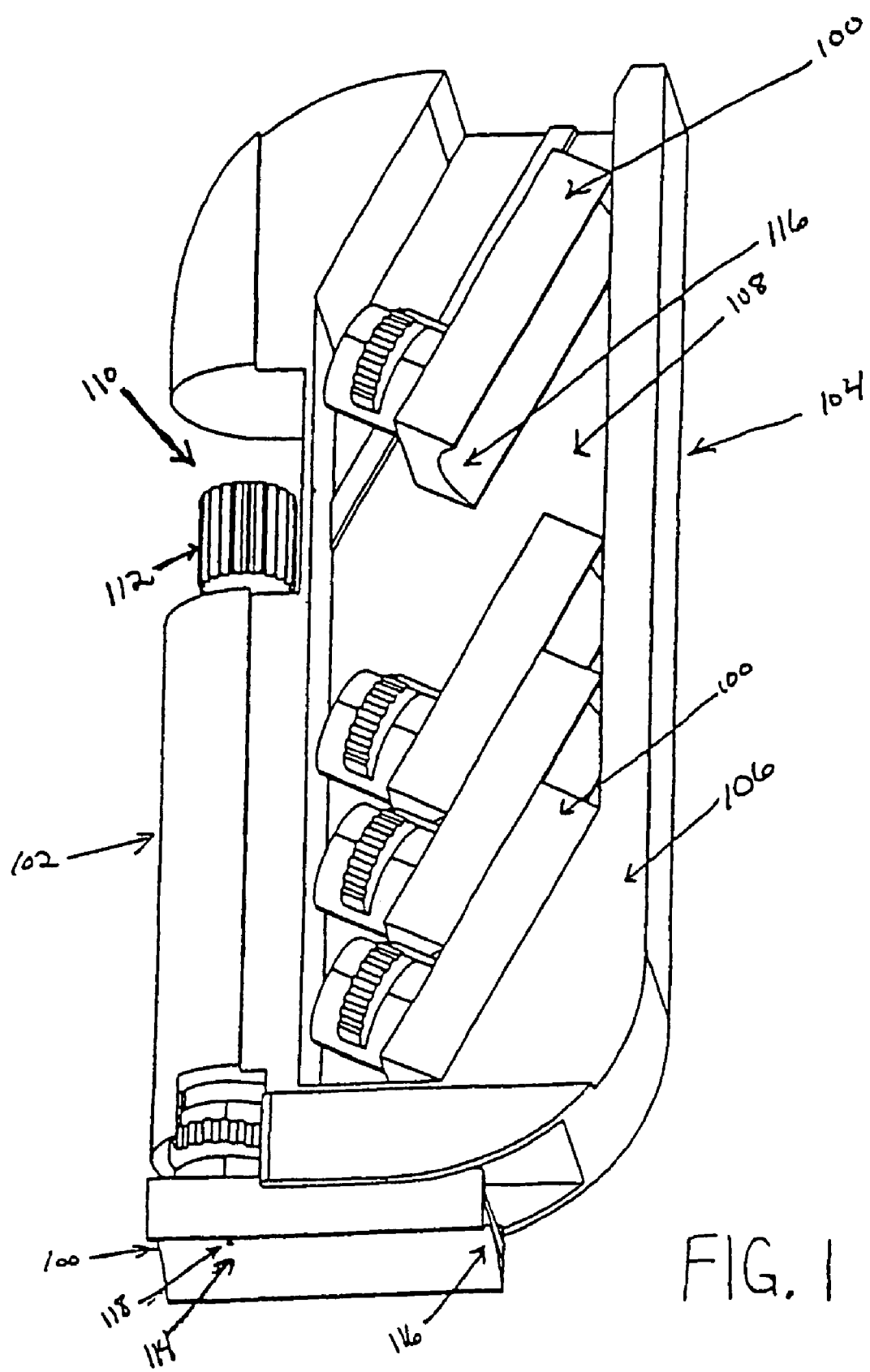
FIG. 1 illustrates a blood sampling system having features of the invention.

Patents U.S. Pat. Nos. 3,030,059, 3,626,929, 4,360,016, 4,608,997, 4,622,974, 4,627,445, 4,637,403, 4,648,408, 4,653,513, 4,873,993, 4,883,068, 4,895,147, 4,920,977, 5,047,044, 5,871,494, 5,971,941 and WO 97/42882 are hereby incorporated by reference in their entirety herein.

Further aspects and advantages of the invention will be set forth in the description which follows, and in part will be obvious from the description, or may become readily apparent through practice of the invention. It is to be understood that both the foregoing general description and the following detailed description are exemplary and explanatory only and are not restrictive of the invention, as claimed.

"Integrated" as used herein means that two or more functions are conducted without intervention by the user: the "integrated" housing contains the mechanism for a plurality of functions, e.g., reproducible lancing, blood sample storage, and (optionally) analysis, the combination of functions occurring as the result a single initiating act by the user (i.e. each function does not have to be separately initiated). The "initiating act" is an action performed by the user which results in a plurality of actions (e.g. blood collection, storage, and analysis) being performed by the blood sampling device without further action required of the user. In the context of a combined lancet driver/sample acquisition module, integrated means that actuation of the lancet driver, lancing of the skin, and sample collection and storage all may occur as the result of a single simple motion (the initiating act) by the user, such as pressing the device against the skin to be sampled. In the context of a sample acquisition module which is configured to be disposable and attached to a reusable lancet driver during use, integrated means that lancing of the skin, sample collection, and sample storage all may occur as the result of a single simple motion by the user, such as pressing the device against the skin to be sampled. If a device is "configured to allow integrated steps A, B, and C", then steps A, B, and C all follow as a result of a single initiating action. "Reproducible" in this context means that the lancing is controlled, having adjustable depth, preload force, and (optionally) opportunity for multiple lancing to assure a sufficient blood sample is obtained: "Preload force" is a measure of the amount of force which must be applied to the skin of the user by the apparatus before triggering the firing of the lancet, and "adjustable preload force" allows the user to select the amount of preload force, in such a manner that the selected amount of preload force will be consistently applied in each successive use of the apparatus unless the user re-adjusts the preload force setting.

"Seamless" as used herein means without substantial exposure to contaminating air: "seamless sampling" thus includes obtaining a blood sample, storing the sample, and (optionally) subjecting the blood sample to analysis without substantial contamination from ambient air. "Substantially" or "substantial" in this context means that the analysis results obtained from the blood sample according to the method or using the apparatus described herein do not deviate by more than about 10%, more preferably 5%, from analysis results obtained using methods that are conventional in the art for analyzing blood samples without contamination from ambient air. "Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

"Testing means" refers to any use, singly or in combination, of chemical test reagents and methods, electrical test circuits and methods, physical test components and methods, optical test components and methods, and biological test reagents and methods to yield information about a blood sample. Such methods are well mown in the art and may be based on teachings of, e.g. Tietz Textbook of Clinical Chemistry, 3d Ed., Sec. V, pp. 776-78 (Burtis & Ashwood, Eds., W. B. Saunders Company, Philadelphia, 1999); U.S. Pat. No. 5,997,817 to Chrismore et al. (Dec. 1, 1999); U.S. Pat. No. 5,059,394 to Phillips et al. (Oct. 22, 1991); U.S. Pat. No. 5,001,054 to Wagner et al. (Mar. 19, 1991); and U.S. Pat. No. 4,392,933 to Nakamura et al. (Jul. 12, 1983), the teachings of which are hereby incorporated by reference, as well as others. The testing means may include sensors in the sample reservoir which test electrochemical properties of the blood, or they may include optical means for sensing optical properties of the blood (e.g. oxygen saturation level), or they may include biochemical reagents (e.g. antibodies) to sense properties (e.g. presence of antigens) of the blood. Said testing means may be present at, e.g., a "test site" or an "analytical site."

"Lancet" means any sharp member used to puncture the skin for the purpose of cutting blood vessels and allowing blood to flow to the surface of the skin. The lancet has certain parameters such as diameter or width to define the cross-sectional area of the member, and geometry to define the shape of the distal or front lancing end of the member. "Lancet driver" means any means for propelling the lancet to puncture the skin. Examples of lancets and lancet drivers are well known in the art and are described herein with relation to the invention.

Miniaturized Lancing and Actuator System

Referring to FIG. 1, a blood sampling system incorporating a disposable sample acquisition module 100, a lancet driver 102, and an optional accessory module 104 are shown. The optional accessory module comprises a case body 106 having a storage cavity 108 for storing sample acquisition modules 100. A cover to this cavity has been left out for clarity. The accessory module further comprises a chamber 110 for holding the lancet driver 102. The lancet driver has a preload adjustment knob 112, by which the trigger point of the lancet driver may be adjusted. This insures a reproducible tension on the surface of the skin for better control of the depth of penetration and blood yield. In one embodiment, the sample acquisition module 100 is removably attached to the lancet driver 102, as shown, so that the sample acquisition module 100 is disposable and the lancet driver 102 is reusable. In an alternative embodiment, the sample acquisition module and lancet driver are contained within a single combined housing, and the combination sample acquisition module/lancet driver is disposable. The sample acquisition module 100 includes a sampling site 114, preferably having a concave depression 116, or cradle, to conform to the shape of a user's finger or other anatomical feature (not shown). The sampling site further includes an opening 118 located in the concave depression. The lancet driver 102 is used to fire a lancet contained within and guided by the sample acquisition module 100 to create an incision on the user's finger when the finger is placed on the sampling site 114. In one embodiment, the sampling site forms a substantially airtight seal at the opening when the skin is firmly pressed against the sampling site; the sampling site may additionally have a soft, compressible material surrounding the opening to further limit contamination of the blood sample by ambient air. "Substantially airtight" in this context means that only a negligible amount of ambient air may leak past the seal under ordinary operating conditions, the substantially airtight seal allowing the blood to be collected seamlessly.

FIG. 2 shows some details of one embodiment of the sample acquisition module. FIG. 2A is a cross section view through line A of FIG. 2B. The lancet 200 is protected in the integrated housing 202 that provides a cradle 204 for positioning the user's finger or other body part, a sampling port 206 within the cradle 204, and a sample reservoir 208 for collecting the resulting blood sample. The lancet 200 is a shaft with a distal end 210 sharpened to produce the incision with minimal pain. The lancet 200 further has an enlarged proximal end 212 opposite the distal end. Similar lancets are commonly known in the art. Rather than being limited to a shaft having a sharp end, the lancet may have a variety of configurations known in the art, with suitable modifications being made to the system to accommodate such other lancet configurations, such configurations having a sharp instrument that exits the sampling port to create a wound from which a blood sample may be obtained. In the figure, the lancet 200 is slidably disposed within a lancet guide 214 in the housing 202, and movement of the lancet 200 within the lancet guide 214 is closely controlled to reduce lateral motion of the lancet, thereby reducing the pain of the lance stick. The sample acquisition module also includes a return stop 228 which retains the lancet within the sample acquisition module. The sample acquisition module has an attachment site 232 for attachment to the lancet driver.

The sample acquisition module further includes a depth selector allowing the user to select one of several penetration depth settings. In FIG. 2, the depth selector is shown as a multi-position thumbwheel 216 having a graduated surface. By rotating the thumbwheel 216, the user selects which part of the graduated surface contacts the enlarged proximal end 212 of the lancet to limit the movement of the lancet 200 within the lancet guide 214. The thumbwheel is maintained in the selected position by a retainer 218 having a protruding, rounded surface which engages at least one of several depressions 220 (e.g. dimples, grooves, or slots) in the thumbwheel 216. The depressions 220 are spatially aligned to correspond with the graduated slope of the thumbwheel 216, so that, when the thumbwheel 216 is turned, the depth setting is selected and maintained by the retainer 218 engaging the depression 220 corresponding to the particular depth setting selected. In alternate embodiments, the retainer may be located on the depth selector and the depressions corresponding to the depth setting located on the housing such that retainer may functionally engage the depressions. Other similar arrangements for maintaining components in alignment are known in the art and may be used. In further alternate embodiments, the depth selector may take the form of a wedge having a graduated slope which contacts the enlarged proximal end of the lancet, with the wedge being retained by a groove in the housing.

The sample reservoir 208 includes an elongate, rounded chamber 222 within the housing 202 of the sample acquisition module. The chamber 222 has a flat or slightly spherical shape, with at least one side of the chamber 222 being formed by a smooth polymer, preferably absent of sharp corners. The sample reservoir 208 also includes an entrance 224 to the chamber 222, which is in fluid communication with the sampling port 206, and a vent 226 exiting the chamber. A cover (not shown), preferably of clear material such as plastic, positions the lancet 200 and closes the chamber 208, forming an opposing side of the chamber 208. In embodiments where the cover is clear, the cover may serve as a testing means whereby the sample may be analyzed in the reservoir via optical sensing techniques operating through the cover. A clear cover will also aid in determining by inspection when the sample reservoir is full of the blood sample.

Figure 3:
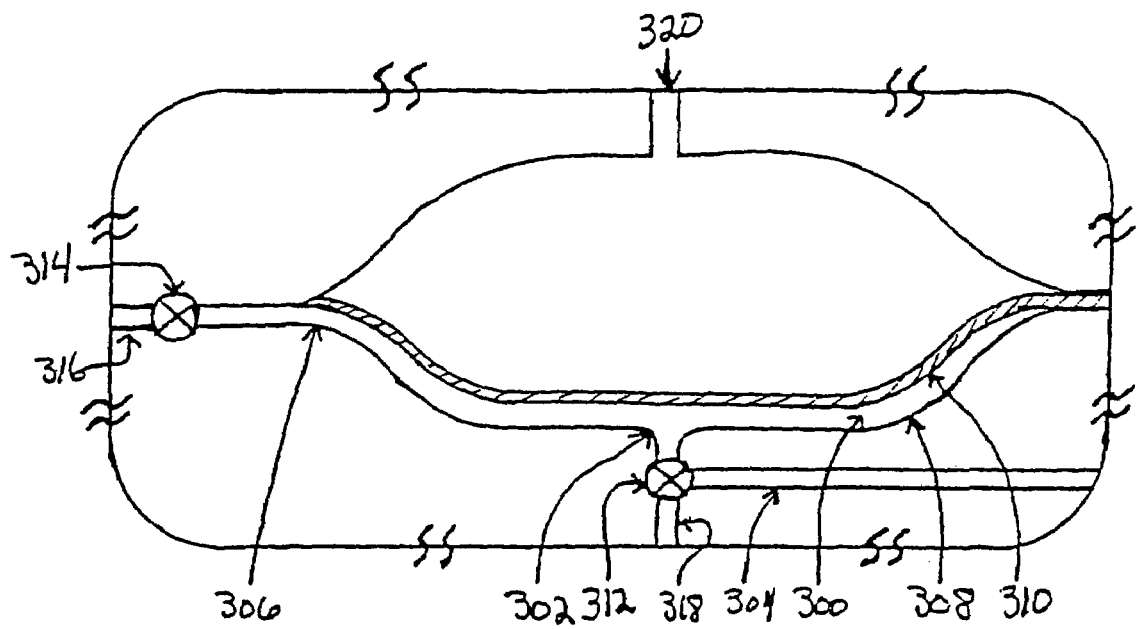
FIG. 3 schematically depicts a portion of the sample acquisition module illustrating an alternate embodiment of the sample reservoir.

FIG. 3 shows a portion of the sample acquisition module illustrating an alternate embodiment of the sample reservoir. The sample reservoir has a chamber 300 having an entrance 302 joining the chamber 300 to a blood transport capillary channel 304; the chamber 300 also has a vent 306. The chamber has a first side 308 that has a flat or slightly spherical shape absent of sharp corners and is formed by a smooth polymer. An elastomeric diaphragm 310 is attached to the perimeter of the chamber 300 and preferably is capable of closely fitting to the first side of the chamber 308. To control direction of blood flow, the sample reservoir is provided with a first check valve 312 located at the entrance 302 of the sample reservoir and a second check valve 314 leading to an exit channel 316 located at the vent 306. Alternately, a single check valve (at the location 312) may be present controlling both flow into the chamber 300 via the blood transport capillary channel 304 and flow out of the chamber 300 into an optional alternate exit channel 318. The sample reservoir has a duct 320 connecting to a source of variable pressure facilitating movement of the diaphragm 310. When the diaphragm 310 is flexed away from the first side of the chamber 308 (low pressure supplied from the source via duct 320), the first check valve 312 is open and the second check valve 314 is closed, aspiration of the blood sample into the sample reservoir follows. When the diaphragm 310 is flexed in the direction of the first side of the chamber 308 (high pressure supplied from the source via duct 320) with the first check valve 312 closed and the second check valve 314 open, the blood is forced out of the chamber 300. The direction of movement and actuation speed of the diaphragm 310 can be controlled by the pressure source, and therefore the flow of the sample can be accelerated or decelerated. This feature allows not only reduced damage to the blood cells but also for the control of the speed by which the chamber 300 is filled. While control of the diaphragm 310 via pneumatic means is described in this embodiment, mechanical means may alternately be used. Essentially, this micro diaphragm pump fulfills the aspiration, storage, and delivery functions. The diaphragm 310 may be used essentially as a pump to facilitate transfer of the blood to reach all areas required. Such required areas might be simple sample storage areas further downstream for assaying or for exposing the blood to a chemical sensor or other testing means. Delivery of the blood may be to sites within the sample acquisition module or to sites outside the sample acquisition module, i.e. a separate analysis device. In an alternate embodiment, a chemical sensor or other testing means is located within the sample acquisition module, and the blood is delivered to the chemical sensor or other testing means via a blood transfer channel in fluid communication with the sample reservoir. The components of the sample acquisition module may be injection molded and the diaphragm may be fused or insertion molded as an integral component.

Figure 4:
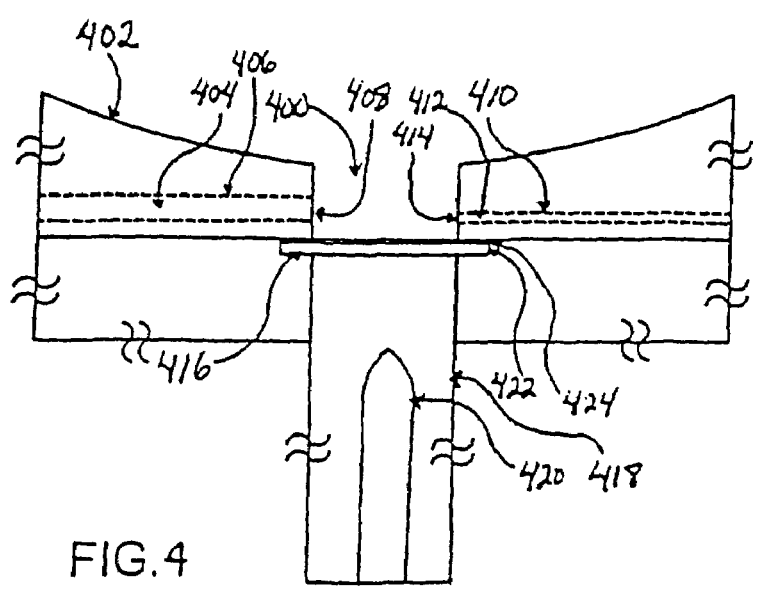
FIG. 4 depicts a portion of the disposable sample acquisition module surrounding the sampling port.

FIG. 4 depicts a portion of the disposable sample acquisition module surrounding the sampling port 400, including a portion of the sampling site cradle surface 402. The housing of the sample acquisition module includes a primary capillary channel 404 connecting the sampling port to the sample reservoir. The primary capillary channel 404 includes a primary channel lumenal surface 406 and a primary channel entrance 408, the primary channel entrance 408 opening into the sampling port 400. The sample acquisition module may optionally include a supplemental capillary channel 410 having a supplemental channel lumenal surface 412 and a supplemental channel entrance 414, the supplemental channel entrance 414 opening into the sampling port 400. The primary capillary channel 404 has a greater cross-sectional area than the supplemental capillary channel 410, preferably by at least a factor of two. Thus, the supplemental capillary channel 410 draws fluid faster than the primary capillary channel 404. When the first droplet of blood is received into the sampling port 400, the majority of this droplet is drawn through the supplemental capillary channel 410. However, as the blood continues to flow from the incision into the sampling port 400, most of this blood is drawn through the primary capillary channel 404, since the supplemental capillary channel 410 is of limited capacity and is filled or mostly filled with the first blood droplet. This dual capillary channel configuration is particularly useful in testing where there is a concern with contamination of the sample, e.g. with debris from the lancet strike or (particularly in the case of blood gas testing) with air.

In order to improve blood droplet flow, some priming or wicking of the surface with blood is at times necessary to begin the capillary flow process. Portions of the surfaces of the sampling port 400 and the primary and supplemental (if present) capillary channels 404, 410 are treated to render those surfaces hydrophilic. The surface modification may be achieved using mechanical, chemical, corona, or plasma treatment. Examples of such coatings and methods are marketed by AST Products (Billerica, Mass.) and Spire Corporation (Bedford, Mass.). However, a complete blanket treatment of the surface could prove detrimental by causing blood to indiscriminately flow all over the surface and not preferentially through the capillary channel(s). This ultimately will result in losses of blood fluid. The particular surfaces which receive the treatment are selected to improve flow of blood from an incised finger on the sampling site cradle surface 402 through the sampling port 400 and at least one of the capillary channels 404, 410 to the sample reservoir. Thus, the treatment process should be masked off and limited only to the selected surfaces. The masking process of selectively modifying the sampling surface from hydrophobic to hydrophilic may be done with mechanical masking techniques such as with metal shielding, deposited dielectric or conductive films, or electrical shielding means. In some embodiments, the treated surfaces are limited to one or more of the following: the surface of the sampling port which lies between the sampling site cradle surface and the primary and supplemental capillary channel, the surface immediately adjacent to the entrances to the primary and/or supplemental capillary channels 408, 414 (both within the sampling port and within the capillary channel), and the lumenal surface of the primary and/or supplemental capillary channels 406, 412. The blood upon exiting the incision preferentially moves through the sampling port 400 into the supplementary capillary channel 410 (if present) and into the primary capillary channel 404 to the sample reservoir, resulting in efficient capture of the blood. Alternatively, the substrate material may be selected to be hydrophilic or hydrophobic, and a portion of the surface of the substrate material may be treated for the opposite characteristic.

Still looking at FIG. 4, in a preferred embodiment, a membrane 416 at the base of the sampling port 400 is positioned between the retracted sharpened distal end of the lancet 418 and the entrance to the capillary channels 408, 414. The membrane 416 facilitates the blood sample flow through the capillary channels 404, 410 by restricting the blood from flowing into the area 418 surrounding the distal end of the lancet 420. The blood thus flows preferentially into the sample reservoir. In an embodiment, the membrane 416 is treated to have a hydrophobic characteristic. In another embodiment, the membrane 416 is made of polymer-based film 422 that has been coated with a silicone-based gel 424. For example, the membrane structure may comprise a polymer-based film 422 composed of polyethylene terephthalate, such as the film sold under the trademark MYLAR. The membrane structure may further comprise a thin coating of a silicone-based gel 424 such as the gel sold under the trademark SYLGARD on at least one surface of the film. The usefulness of such a film is its ability to reseal after the lancet has penetrated it without physically affecting the lancet's cutting tip and edges. The MYLAR film provides structural stability while the thin SYLGARD silicone laminate is flexible enough to retain its form and close over the hole made in the MYLAR film. Other similar materials fulfilling the structural stability and flexibility roles may be used in the manufacture of the membrane in this embodiment.

The membrane 416 operates to allow the sharpened distal end of the lancet 420 to pierce the membrane as the sharpened distal end of the lancet 420 travels into and through the sampling port 400. In the most preferred embodiment, the silicone-based gel 424 of the membrane 416 automatically seals the cut caused by the piercing lancet. Therefore, after an incision is made on a finger of a user, the blood from the incision is prevented from flowing through the membrane 416, which aids the blood to travel through the primary capillary channel 404 to accumulate within the sample reservoir. Thus the film prevents any blood from flowing into the lancet device assembly, and blood contamination and loss into the lancet device mechanism cavity are prevented. Even without the resealing layer 424, the hydrophobic membrane 416 deters the flow of blood across the membrane 416, resulting in improved flow through the primary capillary channel 404 and reduced or eliminated flow through the pierced membrane 416.

Figure 5B:
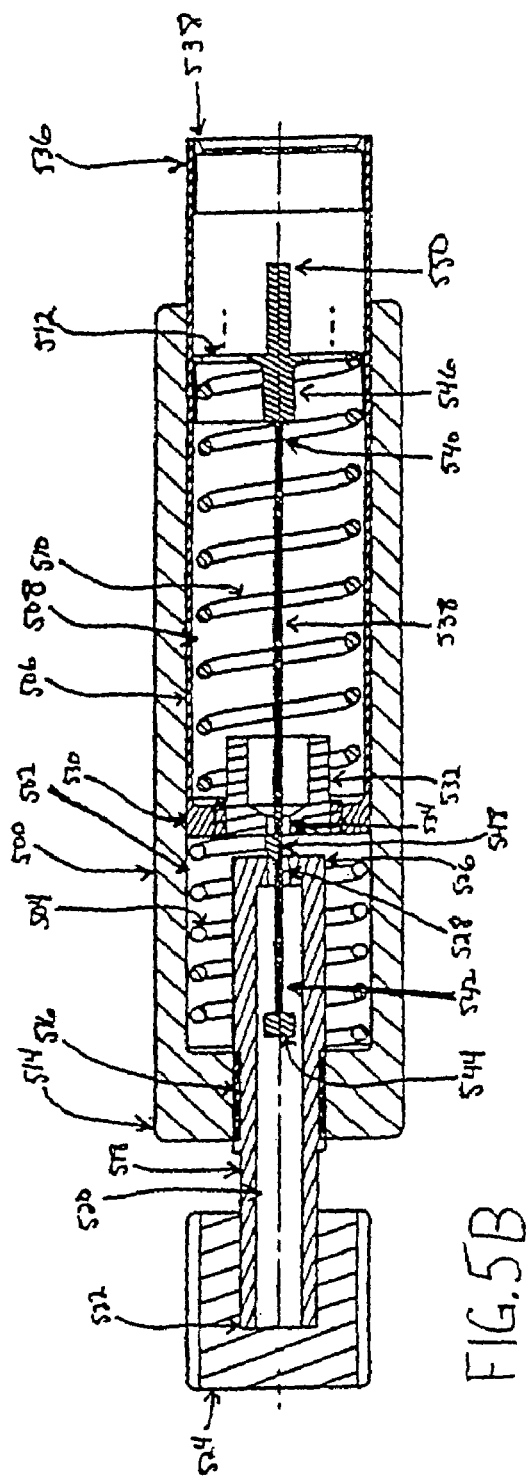
Figure 5C:
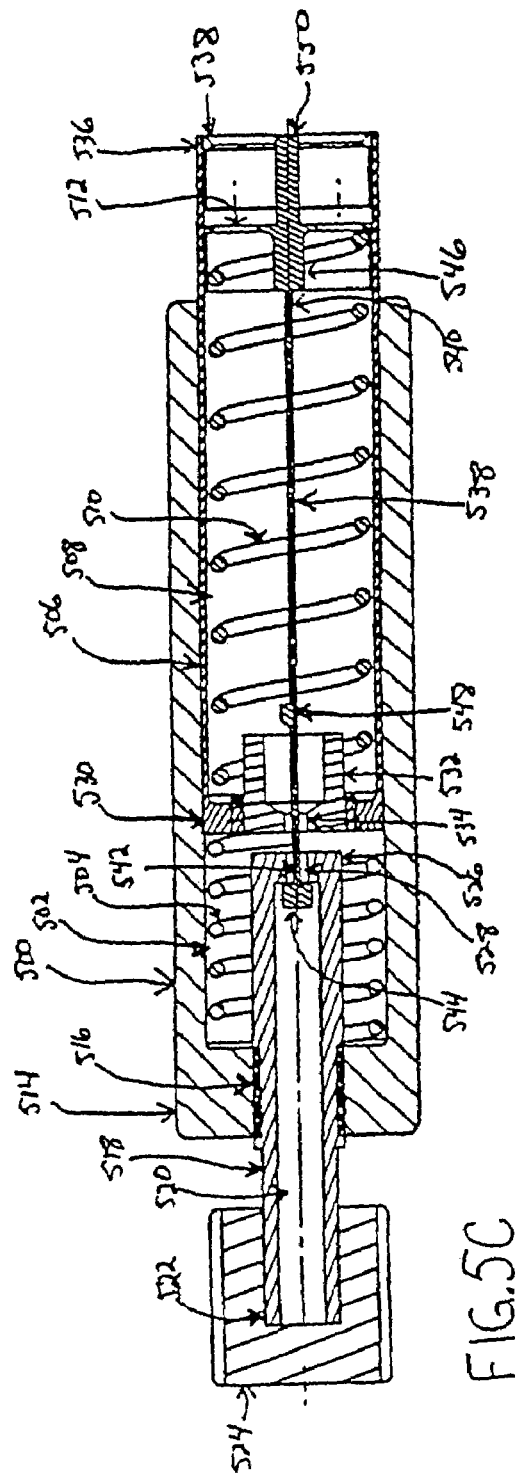

FIGS. 5A, 5B, and 5C illustrate one implementation of the lancet driver at three different points during the use of the lancet driver. In this description of the lancet driver, proximal indicates a position relatively close to the site of attachment of the sample acquisition module; conversely, distal indicates a position relatively far from the site of attachment of the sample acquisition module. The lancet driver has a driver handle body 500 defining a cylindrical well 502 within which is a preload spring 504. Proximal to the preload spring 504 is a driver sleeve 506 which closely fits within and is slidably disposed within the well 502. The driver sleeve 506 defines a cylindrical driver chamber 508 within which is an actuator spring 510. Proximal to the actuator spring 510 is a plunger sleeve 512 which closely fits within and is slidably disposed within the driver sleeve 506.

The driver handle body 500 has a distal end 514 defining a threaded passage 516 into which a preload screw 518 fits. The preload screw defines a counterbore 520. The preload screw 518 has a distal end 522 attached to a preload adjustment knob 524 and a proximal end 526 defining an aperture 528. The driver sleeve 506 has a distal end 530 attached to a catch fitting 532. The catch fitting 532 defines a catch hole 534. The driver sleeve 506 has a proximal end 536 with a sloped ring feature 538 circling the interior surface of the driver sleeve's proximal end 536.

The lancet driver includes a plunger stem 538 having a proximal end 540 and a distal end 542. At its distal end 542, the plunger stem 538 is terminated by an enlarged plunger head 544. At its proximal end 540, the plunger stem 538 is terminated by an enlarged plunger base 546. A plunger hook 548 is located on the plunger stem 538 between the plunger head 544 and the plunger base 546. The plunger base 546 is fixedly attached to the plunger sleeve 512, and the plunger head 544 is slidably disposed within the counterbore 520 defined by the preload screw 518. The plunger stem 538 extends from the plunger head 544, through the aperture 528 defined by the proximal end 526 of the preload screw, thence through the hole 534 in the catch fitting 532, to the plunger base 546. The plunger base 546 extends proximally past the plunger sleeve 512 to form a plunger tip 550. For assembly purposes, the plunger base 546 may be incorporated into the plunger sleeve 512, and the plunger stem 538 attached to the plunger base 546 by crimping, swaging, gluing, welding, or some other means.

The operation of the blood sampling system may be described as follows, with reference to FIGS. 1 through 5. In operation, a fresh sample acquisition module 100 is removed from the storage cavity 108 and adjusted for the desired depth setting using the multi-position thumbwheel 216. The sample acquisition module 100 is then placed onto the end of the lancet driver 102. The preload setting may be checked, but will not change from cycle to cycle once the preferred setting is found; if necessary, the preload setting may be adjusted using the preload adjustment knob 112. The combined sample acquisition module and lancet driver assembly is then pressed against the user's finger (or other selected anatomical feature) in a smooth motion until the preset trigger point is reached. The trigger point corresponds to the amount of preload force that needs to be overcome to actuate the driver to drive the lancet towards the skin. The preload screw allows the preload setting to be adjusted by the user such that a consistent, preset (by the user) amount of preload force is applied to the sampling site 114 each time a lancing is performed.

When the motion to press the assembly against the user's finger is begun (see FIG. 5A), the plunger hook 548 engages catch fitting 532, holding the actuator spring 510 in a cocked position while the force against the finger builds as the driver sleeve 506 continues to compress the preload spring 504. Eventually (see FIG. 5B) the sloped back of the plunger hook 548 slides into the hole 528 in the proximal end of the preload screw 526 and disengages from the catch fitting 532. The plunger sleeve 512 is free to move in a proximal direction once the plunger hook 548 releases, and the plunger sleeve 512 is accelerated by the actuator spring 510 until the plunger tip 550 strikes the enlarged proximal end of the lancet 212. Upon striking the enlarged proximal end of the lancet 212, the plunger tip 550 of the actuated lancet driver reversibly engages the enlarged proximal end of the lancet 212. This may be accomplished by mechanical means, e.g. a fitting attached to the plunger tip 550 that detachably engages a complementary fitting on the enlarged proximal end of the lancet 212, or the enlarged proximal end of the lancet 212 may be coated with an adhesive that adheres to the plunger tip 550 of the actuated lancet driver. Upon being engaged by the plunger tip 550, the lancet 200 slides within the lancet guide 214 with the sharpened distal end of the lancet 210 emerging from the housing 202 through the sampling port 206 to create the incision in the user's finger. At approximately the point where the plunger tip 550 contacts the enlarged proximal end of the lancet 212, the actuator spring 510 is at its relaxed position, and the plunger tip 550 is traveling at its maximum velocity. During the extension stroke, the actuator spring 510 is being extended and is slowing the plunger tip 550 and lancet 200. The end of stroke occurs (see FIG. 5C) when the enlarged proximal end of the lancet 212 strikes the multi-position thumbwheel 216. The direction of movement of the lancet 200 is reversed and the extended actuator spring then quickly retracts the sharpened distal end of the lancet 210 back through the sampling port 206. At the end of the return stroke, the lancet 200 is stripped from the plunger tip 550 by the return stop 228. The adhesive adheres to the return stop 228 retaining the lancet in a safe position.

As blood seeps from the wound, it fills the sampling port 206 and is drawn by capillary action into the sample reservoir 208. In this embodiment, there is no reduced pressure or vacuum at the wound, i.e. the wound is at ambient air pressure, although embodiments which draw the blood sample by suction, e.g. supplied by a syringe or pump, may be used. The vent 226 allows the capillary action to proceed until the entire chamber is filled, and provides a transfer port for analysis of the blood by other instrumentation. The finger is held against the sample acquisition module until a complete sample is observed in the sample reservoir. As the sample acquisition module 100 is removed from the lancet driver 102, a latch 230 that is part of the return stop 228 structure engages a sloped ring feature 538 inside the lancet driver 102. As the lancet driver 102 is removed from the sample acquisition module 100, the latch forces the return stop 228 to rotate toward the lancet 200, bending it to lock it in a safe position, and preventing reuse.

As the sample acquisition module 100 is removed from the lancet driver 102, the driver sleeve 506 is forced to slide in the driver handle body 500 by energy stored in the preload spring 504. The driver sleeve 506, plunger sleeve 512, and actuator spring 510 move outward together until the plunger head 544 on the plunger stem 538 contacts the bottom of the counterbore 520 at the proximal end of the preload screw 526. The preload spring 504 continues to move the driver sleeve 506 outward compressing the actuator spring 510 until the plunger hook 548 passes through the hole 534 in the catch fitting 532. Eventually the two springs reach equilibrium and the plunger sleeve 512 comes to rest in a cocked position.

After the sample acquisition module 100 is removed from the lancet driver 102, it may be placed in a separate analysis device to obtain blood chemistry readings. In a preferred embodiment, the integrated housing 202 or sample reservoir 208 of the sample acquisition module 100 contains at least one biosensor which is powered by and/or read by the separate analysis device. In another embodiment, the analysis device performs an optical analysis of the blood sample directly through the clear plastic cover of the sample acquisition module. Alternatively, the blood sample may be transferred from the sample acquisition module into an analysis device for distribution to various analysis processes.

Alternate embodiments of the invention offer improved success rates for sampling, which reduces the needless sacrifice of a sample storage reservoir or an analysis module due to inadequate volume fill. Alternate embodiments allow automatic verification that sufficient blood has been collected before signaling the user (e.g. by a signal light or an audible beep) that it is okay to remove the skin from the sampling site. In such alternate embodiments, one or more additional lancet(s) (denoted backup lancets) and/or lancet driver(s) (denoted backup lancet drivers) and/or sample reservoir(s) (denoted backup sample reservoirs) are present with the "primary" sample acquisition module. In one such preferred embodiment, following detection of inadequate blood sample volume (e.g., by light or electronic methods), a backup sampling cycle is initiated automatically. The "backup sampling cycle" includes disconnecting the primary sample reservoir via a simple valving system, bringing the backup components online, lancing of the skin, collection of the blood, and movement of the blood to the backup sample reservoir. Blood flows into the backup sample reservoir until the required volume is obtained. The cycle repeats itself, if necessary, until the correct volume is obtained. Only then is the sample reservoir made available as a source of sampled blood for use in measurements or for other applications. The series of reservoirs and/or lancets and/or lancet drivers may easily be manufactured in the same housing and be transparent to the user. In one embodiment, up to three sample reservoirs (the primary plus two backup) are present in a single sample acquisition module, each connected via a capillary channel/valving system to one or more sampling ports. Another embodiment has four sample reservoirs (the primary plus three backup) present in a single sample acquisition module, each connected via a capillary channel/valving system to one or more sampling ports. With three or four sample reservoirs, at least an 80% sampling success rate can be achieved for some embodiments.

Another embodiment includes a miniaturized version of the lancet device. Several of the miniature lancets may be located in a single sampling site, with corresponding capillary channels to transfer blood to one or more reservoirs. The capillary channels may optionally have valves for controlling flow of blood. The device may also include one or more sensors for detecting the presence of blood, e.g. to determine if a sufficient quantity of blood has been obtained. In such an embodiment, the combined blood sampling system—the disposable sample acquisition module, the lancet driver, and the optional accessory module will have dimensions no larger than about 150 mm long, 60 mm wide, and 25 mm thick. In other embodiments, the size of the combined blood sampling system including the disposable sample acquisition module, the lancet driver, and the optional accessory module will have dimensions no larger than about 100 mm long, about 50 mm wide, and about 20 mm thick, and in still other embodiments no larger than about 70 mm long, about 30 mm wide, and about 10 mm thick. The size of the combined blood sampling system including the disposable sample acquisition module, the lancet driver, and the optional accessory module will generally be at least about 10 mm long, about 5 mm wide, and about 2 mm thick.

In another miniature embodiment, the dimensions of the lancet driver without the accessory module or sample acquisition module are no larger than about 80 mm long, 10 mm wide, and 10 mm thick, or specifically no larger than about 50 mm long, 7 mm wide, and 7 mm thick, or even more specifically no larger than about 15 mm long, 5 mm wide, and 3 mm thick; dimensions of the lancet driver without the accessory module or sample acquisition module are generally at least about 1 mm long, 0.1 mm wide, and 0.1 mm thick, or specifically at least about 2 mm long, 0.2 mm wide, and 0.2 mm thick, or more specifically at least about 4 mm long, 0.4 mm wide, and 0.4 mm thick. In yet another miniature embodiment, dimensions of the miniature sample acquisition module without the lancet driver or accessory module are no larger than about 15 mm long, about 10 mm wide, and about 10 mm thick, or no larger than about 10 mm long, about 7 mm wide, and about 7 mm thick, or no larger than about 5 mm long, about 3 mm wide, and about 2 mm thick; dimensions of the miniature sample acquisition module without the lancet driver or accessory module are generally at least about 1 mm long, 0.1 mm wide, and 0.1 mm thick, specifically at least about 2 mm long, 0.2 mm wide, and 0.2 mm thick, or more specifically at least about 4 mm long, 0.4 mm wide, and 0.4 mm thick.

In another embodiment, the miniaturized sample acquisition module and the lancet driver form a single unit having a shared housing, and the combined sample acquisition module/lancet driver unit is disposable. Such a combined unit is no larger than about 80 mm long, about 30 mm wide, and about 10 mm thick, specifically no larger than about 50 mm long, about 20 mm wide, and about 5 mm thick, more specifically, no larger than about 20 mm long, about 5 mm wide, and about 3 mm thick; the combined unit is generally at least about 2 mm long, about 0.3 mm wide, and about 0.2 mm thick, specifically at least about 4 mm long, 0.6 mm wide, and 0.4 mm thick, more specifically, at least about 8 mm long, 1 mm wide, and 0.8 mm thick.

Although the above-described embodiments of the present invention have been described in detail, various modifications to the present invention will become apparent to those skilled in the art from the foregoing description and accompanying drawings and will be within the scope of the invention, which is to be limited only by the following claims.

The invention claimed is:

1. A device for collecting blood from the skin of a patient, the device comprising
    a housing having a sampling site, the sampling site defining an opening and having a concave depression,
    a lancet having a lancet tip adjacent the opening, and
    a lancet driver operably disposed to the lancet to drive the lancet tip through the opening to lance the skin when the lancet driver is actuated,
    a sample acquisition module that includes the lancet, a sample chamber and a biosensor, the sample acquisition module being removably coupled to the lancet driver to provide that the sample acquisition module is disposable and the lancet driver is reusable;
    a manually adjustable penetrating member depth selector positioned at an exterior of the housing, wherein the penetrating member depth selector allows user selection of one of several penetration depth settings to limit penetrating depth of the lancet;
    the device being configured to allow actuation of the lancet driver, lancing of the skin, collection of the blood, and movement of the blood to the sample reservoir to be integrated.

2. The device of claim 1, wherein the sampling site is adapted to conform to the skin of the patient to form a substantially airtight seal at the opening when the skin is firmly pressed against the sampling site.

3. The device of claim 1, further comprising a sampling port and a pierceable membrane, the sampling port having a first end contiguous with the opening and a second end opposite the first end relatively nearer to the lancet tip than the first end, the pierceable membrane adjacent to the second end between the lancet tip and the opening.

4. The device of claim 3, wherein the membrane is resealable.

5. The device of claim 3, wherein the sampling port has a surface, wherein at least a portion of the sampling port surface is hydrophilic.

6. The device of claim 3, wherein the membrane has a surface, wherein at least a portion of the membrane surface is hydrophobic.

7. The device of claim 1, further comprising at least one capillary channel in fluid communication with the opening and the sample reservoir, the capillary channel having a surface, at least a portion of the capillary channel surface being hydrophilic.

8. The device of claim 7, having at least two capillary channels, wherein at least one of the capillary channels is a primary capillary channel and at least one of the capillary channels is a supplemental capillary channel, each capillary channel having a cross-sectional area, wherein the cross-sectional area of the at least one primary capillary channel is at least twice the cross sectional area of the at least one supplemental capillary channel.

9. The device of claim 1, wherein the device further comprises testing means in fluid communication with the opening.

10. The device of claim 1, wherein the device has dimensions smaller than about 80 mm by 30 mm by 10 mm thick.

11. The device of claim 1, further comprising a backup lancet operably disposed to, the sampling site.

12. The device of claim 1, further comprising a backup lancet having a backup lancet tip, the backup lancet maintained within the housing, the sampling site defining a backup opening adjacent the backup lancet tip, the backup opening in fluid communication with the sample reservoir.

13. The device of claim 1, further comprising a backup reservoir in fluid communication with the sampling site.

14. The device of claim 1, further comprising a backup lancet having a backup lancet tip, the backup lancet maintained within the housing, the sampling site defining a backup opening adjacent the backup lancet tip, the sample acquisition module further comprising a backup reservoir in fluid communication with the backup opening.

15. The device of claim 1, wherein the concave depression is dimensioned to form a substantially air tight seal with a finger tip to allow the blood to be collected without substantial contamination from ambient air.

16. A device for collecting blood from the skin of a patient, the device comprising:
 a housing having a sampling site, the sampling site defining an opening and having a concave depression;
 a lancet having a lancet tip adjacent the opening;
 a lancet driver operably disposed to the lancet to drive the lancet tip through the opening to lance the skin when the lancet driver is actuated;
 a sample acquisition module that includes the lancet, a sample chamber and a biosensor, the sample acquisition module being removably coupled to the lancet driver to provide that the sample acquisition module is disposable and the lancet driver is reusable;
 a manually adjustable penetrating member depth selector positioned at an exterior of the housing;
 the device being configured to allow actuation of the lancet driver, lancing of the skin, collection of the blood, and movement of the blood to the sample reservoir to be integrated and;
 at least one capillary channel in fluid communication with the opening and the sample reservoir, the capillary channel having a surface, at least a portion of the capillary channel surface being hydrophilic, wherein the sample reservoir comprises a chamber in fluid communication with the opening, the chamber having a perimeter, and a flexible diaphragm attached to the perimeter of the chamber, the flexible diaphragm capable of moving within the chamber under the influence of a pressure source, said movement of the diaphragm serving to facilitate transport of the blood through the at least one capillary channel.

* * * * *